(12) United States Patent
Orozco et al.

(10) Patent No.: US 12,163,118 B2
(45) Date of Patent: Dec. 10, 2024

(54) CONTINUOUS FLOW REACTOR FOR VIRAL INACTIVATION

(71) Applicant: Boehringer Ingelheim International GmbH, Ingelheim am Rhein (DE)

(72) Inventors: Raquel Orozco, Richmond, CA (US); Jonathan Coffman, Gaithersbury, CA (US); Stephanie Parker, Rialto, CA (US); Natira Gnat Matthews, Redwood City, CA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 845 days.

(21) Appl. No.: 17/283,285

(22) PCT Filed: Oct. 7, 2019

(86) PCT No.: PCT/US2019/054965
§ 371 (c)(1),
(2) Date: Apr. 7, 2021

(87) PCT Pub. No.: WO2020/076683
PCT Pub. Date: Apr. 16, 2020

(65) Prior Publication Data
US 2021/0388308 A1    Dec. 16, 2021

Related U.S. Application Data

(60) Provisional application No. 62/742,530, filed on Oct. 8, 2018.

(51) Int. Cl.
*C12M 1/12* (2006.01)
*C12M 1/00* (2006.01)
*C12N 7/00* (2006.01)

(52) U.S. Cl.
CPC ............ *C12M 47/12* (2013.01); *C12M 23/06* (2013.01); *C12N 7/00* (2013.01)

(58) Field of Classification Search
CPC ...... C12M 47/12; C12M 23/06; C12M 23/26; C12N 7/00
USPC ........................................................ 422/600
See application file for complete search history.

(56) References Cited

U.S. PATENT DOCUMENTS

| | | |
|---|---|---|
| 4,422,773 A | 12/1983 | Cassaday et al. |
| 6,399,031 B1 | 6/2002 | Herrmann et al. |
| 8,377,375 B2 | 2/2013 | Anderle et al. |
| 8,602,636 B2 | 12/2013 | Kauling et al. |

(Continued)

FOREIGN PATENT DOCUMENTS

| | | | |
|---|---|---|---|
| CN | 2607522 Y | 3/2004 | |
| EP | 0045558 A1 * | 10/1982 | ............... B01F 5/00 |

(Continued)

OTHER PUBLICATIONS

International Search Report and Written Opinion for corresponding application, PCT/US2019/054965, date of mailing Jan. 2, 2020.

(Continued)

*Primary Examiner* — Huy Tram Nguyen
(74) *Attorney, Agent, or Firm* — Shelley A. Jones

(57) ABSTRACT

A continuous flow reactor having a plurality of interwoven flow paths in fluid communication to form a single continuous flow reactor tube having a single flow path.

21 Claims, 25 Drawing Sheets

(56) References Cited

U.S. PATENT DOCUMENTS

| | | |
|---|---|---|
| 9,403,138 B2 | 8/2016 | Whittenberger et al. |
| 2006/0153755 A1 | 7/2006 | Obuchi et al. |
| 2006/0162912 A1 | 7/2006 | Prasad Nigam |
| 2007/0000646 A1 | 1/2007 | Chen et al. |
| 2007/0274882 A1 | 11/2007 | Mosler et al. |
| 2008/0075627 A1 | 3/2008 | Garin et al. |
| 2016/0375159 A1 | 12/2016 | Lobedann et al. |
| 2021/0388323 A1 | 12/2021 | Brown et al. |

FOREIGN PATENT DOCUMENTS

| | | |
|---|---|---|
| WO | 199814268 A1 | 4/1998 |
| WO | 199904892 A1 | 2/1999 |
| WO | 2016041896 A1 | 3/2016 |
| WO | 2017129771 A1 | 8/2017 |

OTHER PUBLICATIONS

Orozcp et.al., "Design construction, and optimization of a novel, modular, and scalable incubation chamber for continuous viral inactivation", 2017, Biotechnology Progress, 2017, vol. 33, No. 4, pp. 954-965.

Parker et.al., "Design of a novel continuous flow reactor for low pH viral inactivation", Biotechnology and Bioengineering, 2018, vol. 115, No. 3, pp. 606-616.

Abstract in English for CN2607522, Mar. 24, 2004.

\* cited by examiner

CONTINUOUS FLOW REACTOR FOR VIRAL INACTIVATION

FIELD OF THE INVENTION

The present disclosure generally relates to an apparatus and a process for a continuous flow reactor. More particularly, the present disclosure relates to an apparatus and a process for a continuous flow reactor having at least two turns on a single longitudinal axis, each turn disposed in a different, non-parallel plane.

BACKGROUND OF THE INVENTION

The invention lies on the field of production of biological products like proteins which usually takes place in a bioreactor (fermenter) where e.g. eukaryotic cells are cultivated to produce a protein of interest. Different technologies are established therefore, e.g. fed-batch or continuous or perfusion fermentation. Before use the product needs to be purified. Among the purification steps inactivation of viruses is mandatory, esp. when the product is intended for use in humans.

Presently, virus inactivation at a low pH is performed in a batch reactor. The material to be inactivated (i.e., a liquid which potentially contains the active viruses) is introduced into a batch reactor. The material to be inactivated is brought to a pH of ≤4 by an acidic solution and allowed to stand for the required time. The inactivation of the viruses is effected by contact of the viruses with the acidic solution for a particular product- and process-dependent time. The entire content of the batch reactor experiences inactivation with a virtually identical residence time. Additionally, the virus reduction achieved in each batch is virtually identical.

SUMMARY OF THE INVENTION

In an aspect, a continuous flow reactor is provided. The continuous flow reactor includes a plurality of interwoven flow paths in fluid communication to form a single continuous flow reactor tube having a single flow path.

In another aspect, each of the plurality of interwoven flow paths comprises a plurality of turns that are in different, non-parallel planes.

In a further aspect, the plurality of turns includes at least a first pattern and a second pattern different from the first pattern, wherein the first pattern includes a predetermined number of turns, and the second pattern includes a predetermined number of turns, and wherein the predetermined number of turns in the first pattern is same or different from the predetermined number of turns in the second pattern.

In an aspect, the plurality of turns includes a repeated pattern of turns.

In another aspect, the pattern of turns is repeated after 8 bends.

In a further aspect, each of the plurality of turns includes an angle of from about 100° to about 200°.

In an aspect, each of the plurality of turns includes an angle of from about 135° to about 140°.

In another aspect, the plurality of turns follows a three-dimensional path that includes flow direction changes at approximately 45°, at a turn center.

In a further aspect, the plurality of interwoven flow paths is made of at least one of flexible and memory alloy.

In an aspect, the plurality of interwoven flow paths includes from about 19.6 to about 39.2 turns per 1 m$^3$.

In another aspect, the plurality of interwoven flow paths includes internals.

In a further aspect, the plurality of interwoven flow paths comprises a weft-like pattern and a warp-like pattern.

In an aspect, the plurality of interwoven flow paths comprises a plural bends each bend being rotated, with respect to one another, at an angle around a longitudinal axis of the plurality of interwoven flow paths.

In another aspect, the angle around the longitudinal axis of the interwoven flow path is from about 25 degrees to about 60 degrees.

In an aspect, a continuous flow reactor is provided. The continuous flow reactor at least one flow path on a single longitudinal axis and comprising a plurality of turns, wherein at least two of the plurality of turns are in different, non-parallel planes.

In another aspect, the plurality of turns includes a first pattern that is repeated a predetermined number of times.

In a further aspect, the plurality of turns includes at least a first pattern and a second pattern different from the first pattern, wherein the first pattern includes a predetermined number of turns, and the second pattern includes a predetermined number of turns, and wherein the predetermined number of turns in the first pattern is same or different from the predetermined number of turns in the second pattern.

In an aspect, each of the plurality of turns is separated from one another by a bend having an angle smaller than an angle of the plurality of turns.

In another aspect, each of the bends includes an angle of less than about 135° and wherein each of the plurality of turns includes an angle of from about 135° to about 140°.

In a further aspect, the at least one flow path comprises four flow paths interwoven with one another.

In an aspect, a method of viral inactivation in a continuous flow reactor is provided. The method includes a process stream and at least one virus inactivating compound or solution into a continuous flow reactor at a flow rate having a Reynolds number of from about 187 to about 333 and a Dean Number of from about 105 to about 212; and contacting the process stream with the at least one virus inactivating compound or solution in the continuous flow reactor.

In another aspect, a process for a continuous low pH of viral inactivation of a product stream is provided.

Additional features and advantages of various embodiments will be set forth, in part, in the description that follows, and will, in part, be apparent from the description, or may be learned by the practice of various embodiments. The objectives and other advantages of various embodiments will be realized and attained by means of the elements and combinations particularly pointed out in the description herein.

BRIEF DESCRIPTION OF THE DRAWINGS

The present disclosure in its several aspects and embodiments can be more fully understood from the detailed description and the accompanying drawings, wherein.

Throughout this specification and figures like reference numbers identify like elements.

DETAILED DESCRIPTION OF THE INVENTION

It is to be understood that both the foregoing general description and the following detailed description are exemplary and explanatory only, and are intended to provide an explanation of various embodiments of the present teachings.

Viral safety is mandated for protein therapeutics produced in mammalian cells, and viral clearance procedures are highly regulated. Viruses can be inactivated by adding a compound or a solution to a process stream. Such a compound or solution can include at least one of solvents, detergents, pasteurization (heating), and pH reduction (acids). Low pH is a highly effective method used in monoclonal antibody purification processes, consistently clearing greater than 4 log(10) of large enveloped viruses, including endogenous retroviruses. The American Society for Testing and Materials (ASTM) Standard Practice for Process for Inactivation of Retrovirus by pH prescribes the following conditions for low pH viral inactivation: pH ≤3.6, at ≥15° C., for ≥30 min in a system-specific buffer at the specified pH, providing ≥5 log reduction value (LRV).

Referring to FIGS. 1A-1E, to inactivate viruses, in a process stream, the process stream can be introduced into a continuous flow reactor such as a continuous viral inactivation (CVI) reactor 100. Some exemplary process streams include, but are not limited to, a bioreactor effluent, an anion exchange chromatography effluent, a cation exchange chromatography effluent, an effluent from an aqueous two-phase extraction, an effluent from a precipitation reaction, an effluent from a membrane filtration step, and an effluent from an ultrafiltration step.

Figure 1A:
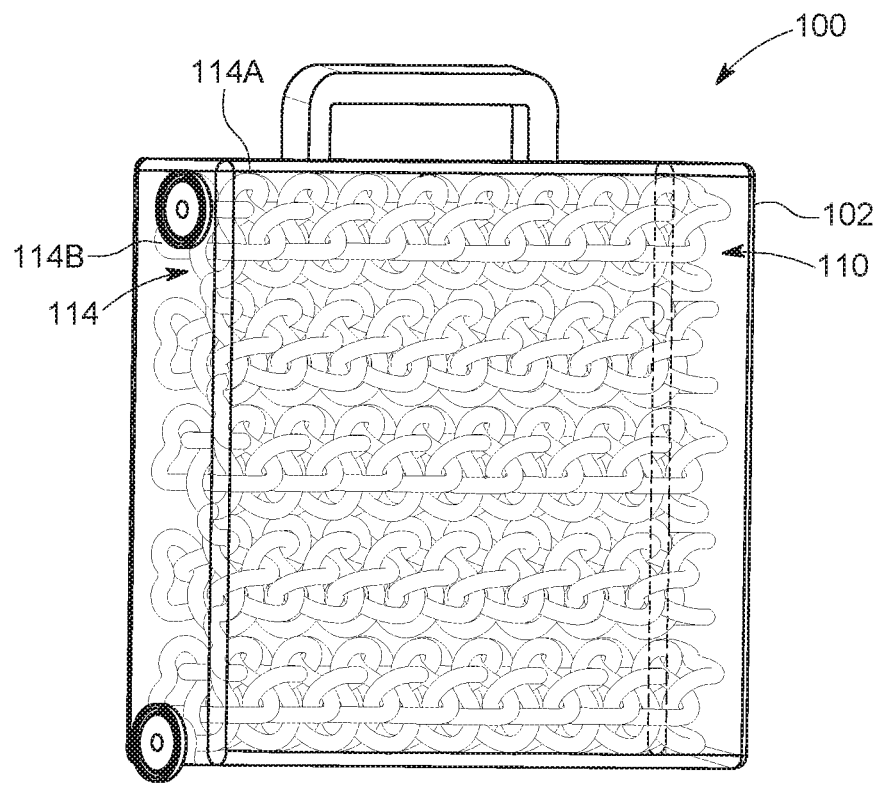
FIG. 1A is a perspective view of a continuous flow reactor showing its casing and exemplary reactor tube, according to an example of the present disclosure.
Figure 1B:
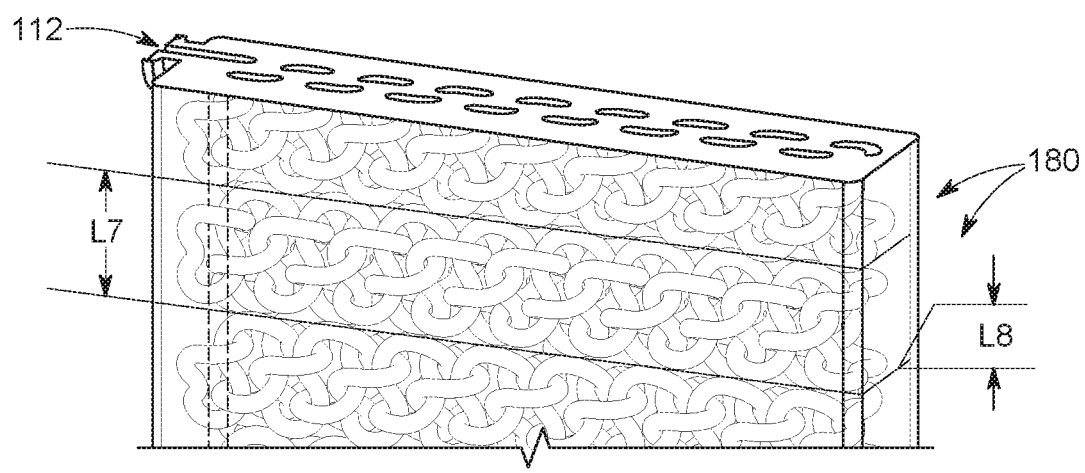
FIG. 1B is a partial perspective view of the continuous tubular reactor of FIG. 1A, according to an example of the present disclosure.
Figure 2A:
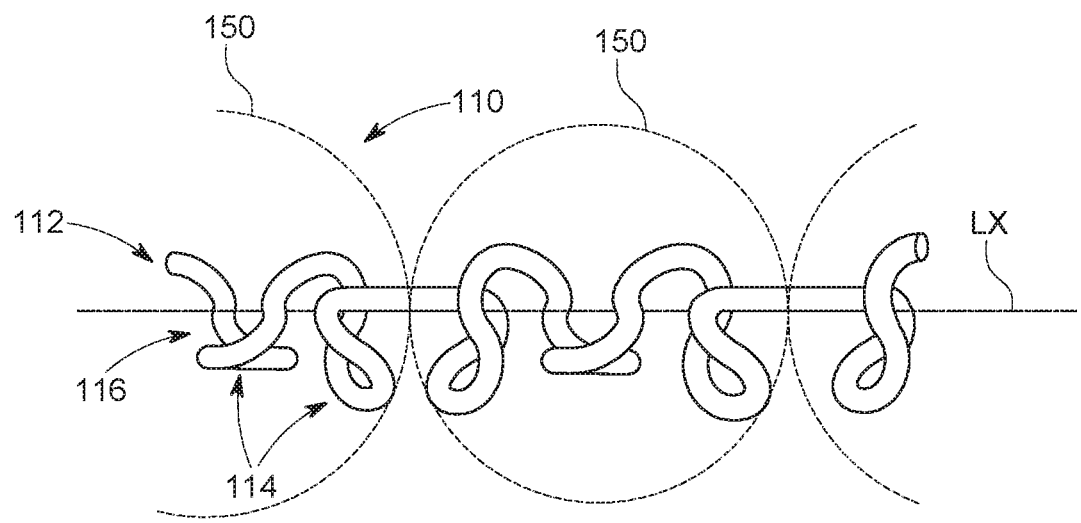
FIG. 2A is an isometric view of an exemplary continuous flow reactor tube having a single run, according to an example of the present disclosure.
Figure 2B:
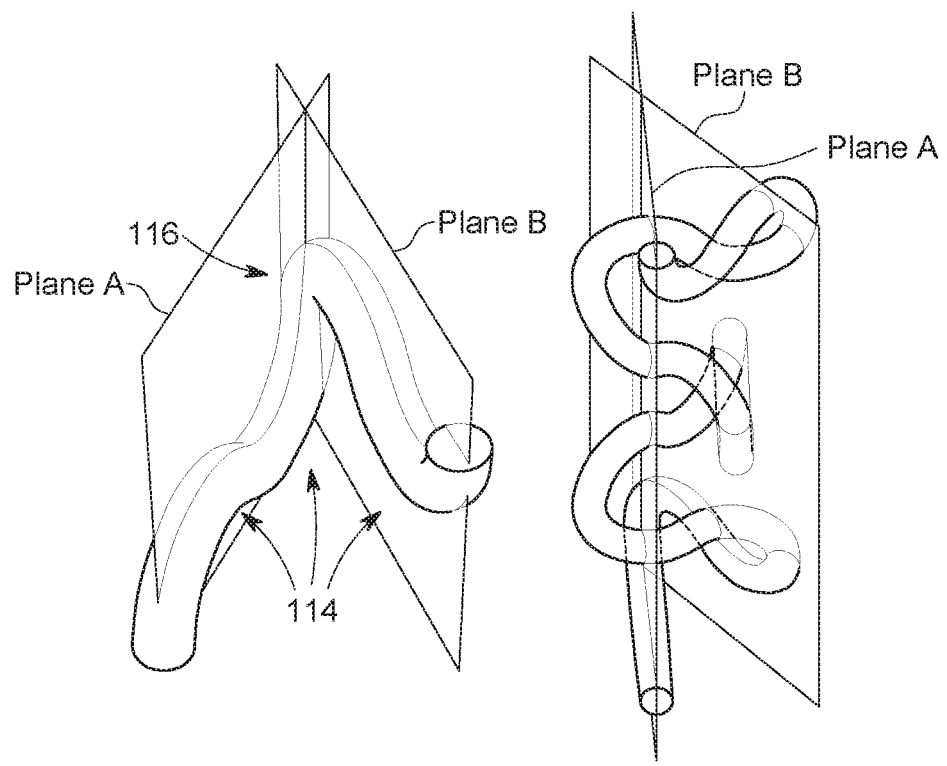
FIG. 2B illustrates the continuous flow reactor tube of FIG. 2A having turns on a single longitudinal axis, but in different, non-parallel planes, according to an example of the present disclosure.

In an example, shown in FIG. 1A, the CVI reactor 100 can be configured to or designed to minimize and/or reduce pressure drop and axial dispersion. Accordingly, the CVI reactor 100 can operate in low Reynolds (Re) number, which is defined as a flow having a Re number of less than 2000 and defined as Re=$\rho vd/\mu$, where $\rho$ is density, v is average velocity, d is the tube diameter, and $\mu$ is dynamic viscosity. For example, the calculation of Re number can be based on a process stream having a temperature of 25° C., $\rho$=1000 kg m-3 and $\mu$=8.9E-4 Pa·s. However, laminar flow can cause axial dispersion, as it is characterized by a parabolic velocity profile, where fluid elements at the center of the tube travel faster than the elements near the wall, resulting in a broad Residence Time Distribution (RTD). As shown in FIGS. 1B, 2A, and 2B, to reduce and/or at least partially eliminate axial dispersion, the CVI reactor 100 can include a flow path or channel 112 having at least two turns or curves 114, such as turns 114A and 114B, which are disposed on a single longitudinal axis LX, but are in different, non-parallel planes (e.g., Plane A and Plane B). This particular design can produce secondary flows that enhance radial mixing and reduce axial dispersion.

A radius of curvature (ROC) of the turn or curve 114 can be determined as a function of the Dean Number (D) and the ratio of the turn length to length of a toric geometry ($L_{DT}$), wherein $D=Re\sqrt{(d/2R)}$, were d is the tube inner diameter and R is the radius of curvature of the flow path, and wherein $L_{DT}=0.322 \times d_c^{0.31} \times Re^{0.59} \times d_i^{0.76}$, where $d_i$ is the internal diameter and $d_c$ is the coil diameter in meters.

Reactor Design

FIGS. 1A-1E illustrate an exemplary CVI reactor 100. The CVI reactor 100 can include a body 102 and a continuous flow reactor tube 110 within the body 102.

As shown in FIG. 1A, the CVI reactor 100 can include a plurality of rows of continuous flow reactor tube 110, such as at least five rows of continuous flow reactor tube 110. In this exemplary CVI reactor 100, the number of turns in each row of continuous flow reactor tube 110 can depend on the external and/or internal diameter of the reactor tube 110. For example, a larger diameter reactor tube 110 may include fewer turns than a smaller diameter reactor tube 110. In one example, when the continuous flow reactor tube 110 includes an ROC of from about 0.3 cm or less to about 2 cm or more, such as from about 1.05 cm, each row of the continuous flow reactor tube 110 can include 16 turns for a total of approximately 320 turns or more. The parameters of the CVI reactor 100 can correspond to a Dean No. of about 50 or more, such as a Dean No. of about 100 or more, for example, a Dean No. of from about 100 to about 500.

In an example, prior to introducing the process stream and at least one virus inactivating compound or solution into the CVI reactor 100, the combined process stream and virus inactivating compound or solution can include a flow rate having a Reynolds number of from about 187 to about 333 and a Dean Number of from about 105 to about 212.

Figure 1C:
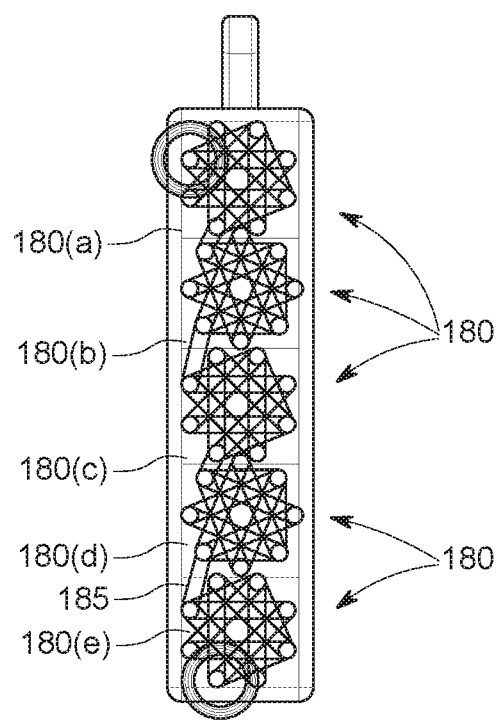
FIG. 1C is a back view of the continuous tubular reactor of FIG. 1A, according to an example of the present disclosure.

The CVI reactor 100 can include about 50 turns or more, such as about 100 turns or more. For example, the CVI rector can include about 320 turns. Referring to FIGS. 1B and 1C, to accommodate approximately 320 turns into a compact design, the flow path 112 in the CVI reactor 100 can be arranged horizontally into a plurality of stacked layers 180, such as from 2 layers 180 to 10 layers 180 or more, for example, 5 layers 180, as shown in FIG. 1C. In an example, flow patch 112 in each layer 180(*a*)-180(*e*) in the stacked layers 180 can include from about 28 turns or less to about 68 turns or more. For example, each layer 180(*a*)-180(*e*) in the stacked layers 180 can include 64 turns. In an example, each layer 180 can be connected to its adjacent lower layer 180 by a 180° turn 185. In an example, where the CVI reactor 100 includes 5 layers 180, the continuous flow reactor tube 110 in each of the 5 layers 180 can be connected to one another by 4 180° vertical turns 185.

Referring to FIG. 1B, in an example, each layer 180 in the CVI reactor 100 can include a depth L7. The depth L7 can be a distance in which a continuous flow reactor tube 110 can be contained therein. At a minimum, the depth L7 can be a distance from a center of the first eight-pointed star in a first layer 180(*a*) to the center of the second eight-pointed star in the second layer 180(*b*). For example, the depth L7 can be defined as a function of the diameter of the continuous reactor tube 110 or the length L3 (shown in FIG. 3C) of an intertwined continuous flow reactor tube 110. In an example, the depth L7 can be about 6.06 times the size of the diameter of the continuous flow reactor tube 110 (i.e., 6.06*d) or less to about 7.84 times the size of the diameter of the continuous flow reactor tube 110 (i.e., 7.84*d). For example, L7 can be about 3.85 cm or less to about 5 cm or more, for example, about 4.7 cm. In an example, the distance L8 can be from the bottom portion of the tubular flow path 112 in a first layer to the top portion of the tubular flow path 112 in a second layer directly below the first layer. The distance of L8 can also be defined as a function of the diameter of the continuous reactor tube 110. In an example, the distance L8 can be from about 0.23 time the size of the diameter of the continuous flow reactor tube 110 (i.e., 0.23*d) to about 0.70 times the size of the diameter of the continuous flow reactor tube 110 (i.e., 0.7*d). For example, L8 can be from about 0.15 cm (1.5 mm) to about 0.5 cm (5 mm), for example, it can be from about 0.425 cm (4.25 mm).

Figure 1D:
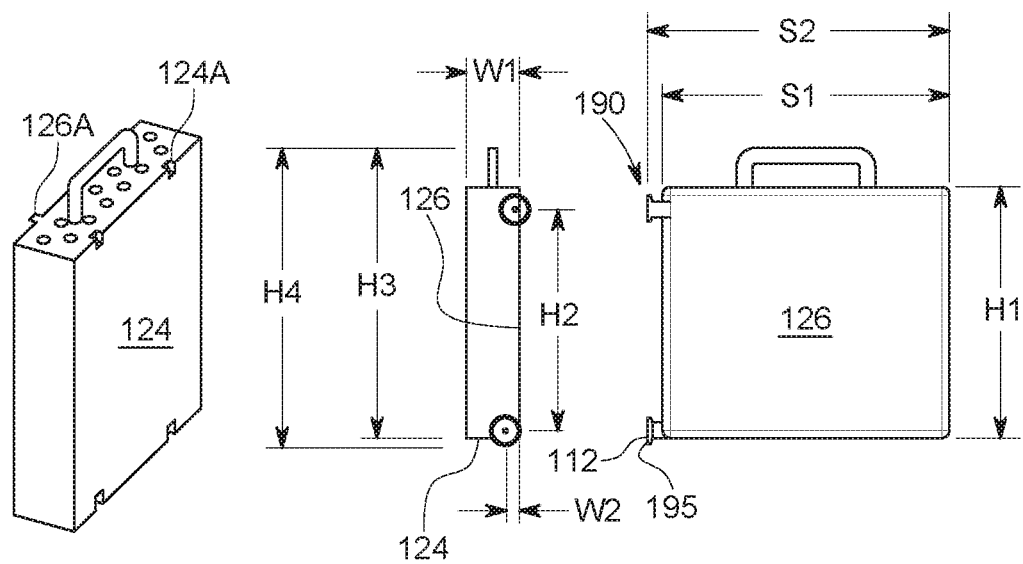
FIG. 1D illustrates the perspective view, front view, and side view of the continuous flow reactor of FIG. 1A, according to an example of the present disclosure.

Referring to FIG. 1D, in an example, CVI reactor 100 can include a body or footprint dimensions L (shown as Si in FIG. 1D)×W (shown as W1 in FIG. 1D)×H (shown as H1 in FIG. 1D) of from about 20×4.5×15 to about 40×9×30 cm, such as about 27×5.8×23.5 cm, and can contain a flow path 112 length of approximately from about 442.6 cm to about 7000 cm, such as about 1770.43 cm, resulting in approximately a flow volume of from about 300 ml to about 800 ml, such as about 560.68 ml. The body of the CVI reactor 100 can include a first side 124 and a second side 126. In an example, the first side 124 can include at least one groove or indentation 124A and the second side 126 can include at least one protrusion 126A. The at least one indentation 124A and the at least one protrusion 126A can be arranged such that when two CVI reactors 100 are positioned abutting to one another, they can be removably secured to one another.

The distance between from the center of the entry point to the exit point of the reactor, indicated as H2, can be from about 5 cm or less to about 200 cm or more, such as from about 15 cm to about 25 cm such as about 23.5 cm. The CVI reactor 100 can also include a length from the bottom of the reactor to the handle, indicated as H3. The length of H3 can be from about 23 cm to about 30 cm, such as about 27.2 cm. In an example, the flange 195 can extend from about 0.1 to about 1 cm, such as about 0.67 cm, from the bottom of the CVI reactor 100. Furthermore, the flange 195 can include a radius of from about 0.3 cm to about 2 cm, such as about 1.1 cm.

In an example, the continuous flow reactor tube 110 can include one or more internals. Internals can include, for example, diffusers, catchers, distributors, catalysts, mixers, redistribution, and collectors to name a few. One or more of these internals can be disposed anywhere and positioned in any manner within the continuous flow reactor tube 110.

In an example, the CVI reactor 100 can include a sampling port (not shown in the Figs.) positioned anywhere through the length of the continuous flow reactor tube 110. For example, the sampling port can be positioned at about halfway between the start and the end of the continuous flow reactor tube 110. The sampling port can be used to extract a sample of the mixed process stream and the virus inactivating compound or solution to determine, for example, the pH level or the consistency of the mixture, and/or any other properties of the mixture. To adjust the pH level, the CVI reactor 100 can include an auxiliary input port. The auxiliary input port will allow the user to add any necessary additional virus inactivating compound or solution or process stream.

In an example, to accommodate smaller or larger volume process stream, a smaller or larger reactor can be used wherein the reactor tube in the smaller or larger reactor includes substantially similar internal diameter to 2*radius of curvature as the reactor 100.

FIGS. 2A-3D illustrate an exemplary continuous flow reactor tube 110 that can operate at low Re. The continuous flow reactor tube 110 can include the tubular flow path 112 that includes turns or curves 114 and bends 116. At least two of the turns or curves 114 are disposed on a single longitudinal axis LX, but in a different, non-parallel planes, for example, plane A and plane B. Depending on the number of paths used to create the continuous flow reactor tube 110, the turns can be in two or more different, non-parallel planes, such as from about 6 to about 13 different planes, for example, 8 different planes. Furthermore, at least two of the turns are arranged such that the planes corresponding to the at least two turns can intersect one another, as shown, for example, in FIGS. 2B and 3B. The turns can also create a pattern that can be repeated or not repeated after a predetermined number of turns. For Example, as shown in FIG. 2D, which illustrates a cross-section of a single path along its longitudinal axis, the single path can include a pattern 150 that is repeated at least two times (see also FIG. 2A). Each flow path can include from about 4 turns to about 128 turns or more of alternating turns, such as about 16 to about 32 turns. Each turn 114 can include an angle of from about 110° to about 280°, such as about 135° to about 140°. In an example, the first turn can include an angle (such as an angle of about 135°) that is smaller than the angle of the second turn (such as an angle of about 140°). Additionally, as shown in FIGS. 2A, 2B, and 3A, each flow path can also include from about 8 to about 64 or more bends 116, such as from about 8 to about 16 bends 116. Each bend 116 can include an angle of from about 15° to less than about 135°, for example, an angle of from about 30° to about 90°, such as an angle of about 45°. In an example, each pattern 150 can be repeated after about 4 bends or more, such as after about 8 bends.

In another example, not shown in the figures, a path of the continuous flow reactor tube 110 can include two or more different patterns, which may or may not be repeated. When the continuous flow reactor tube 110 includes a plurality of interwoven flow paths, each path of the continuous flow reactor tube 110 can include a substantially similar pattern. Alternatively, or additionally, each path of the continuous flow reactor tube 110 can include a different pattern. Moreover, each path of the continuous flow reactor tube 110 can include a similar number of repeated patterns (for example two similarly repeated patterns) or can include more or less than two repeated patterns. For example, the second path can include two similarly repeated patterns or can include three similarly repeated patterns.

As discussed above, the interwoven tubular flow path of the weave design consists of alternating 135°-140° turns with 45° bends at the center of each turn, as shown in FIG. 2B. The inner diameter of the flow path can be from about 0.3 cm or less to about 1 cm or more, for example from about 0.6 cm to about 0.7 cm, such as an inner diameter of about 0.635 cm. Furthermore, the minimum radius of curvature of the 130-140° turns can be from about 0.3 cm to about 2 cm, such as about 1.05 cm, determined for an ID of 0.635 cm.

Figure 2C:
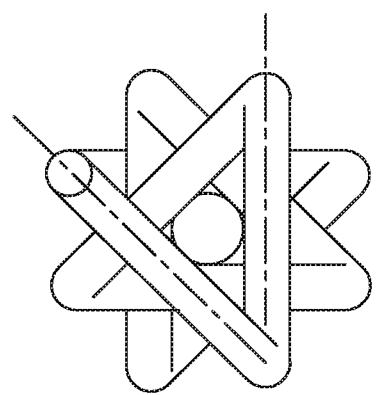
FIG. 2C is a top view of the exemplary continuous flow tube of FIG. 2A, according to an example of the present disclosure.
Figure 2D:
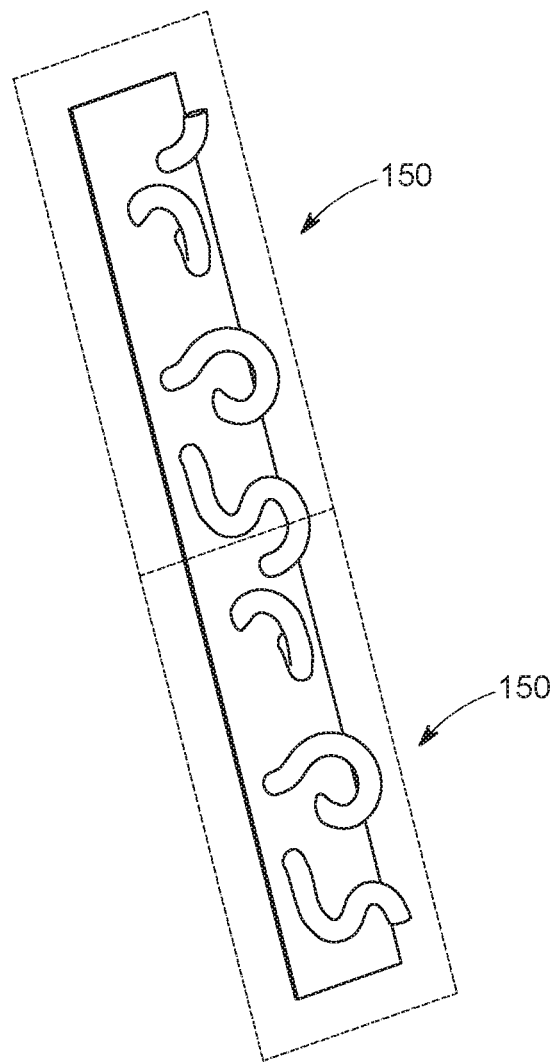
FIG. 2D is a cross-sectional view along the longitudinal access of the tube of FIG. 2A, according to an example of the present disclosure.
Figure 2E:
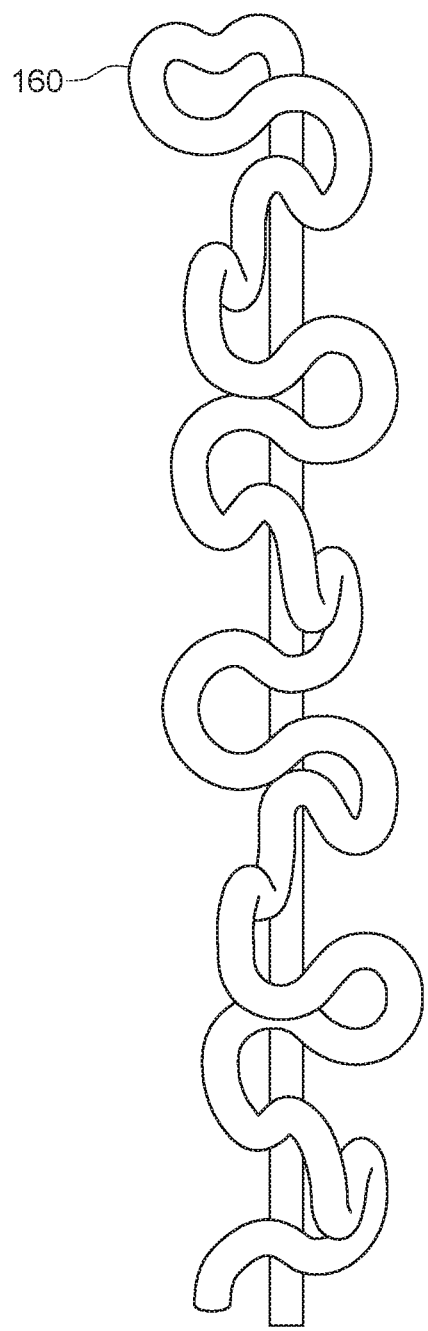
FIG. 2E is the continuous flow reactor tube of FIG. 2A having a first flow path with turns and a second path that is substantially straight, according to an example of the present disclosure.
Figure 3A:
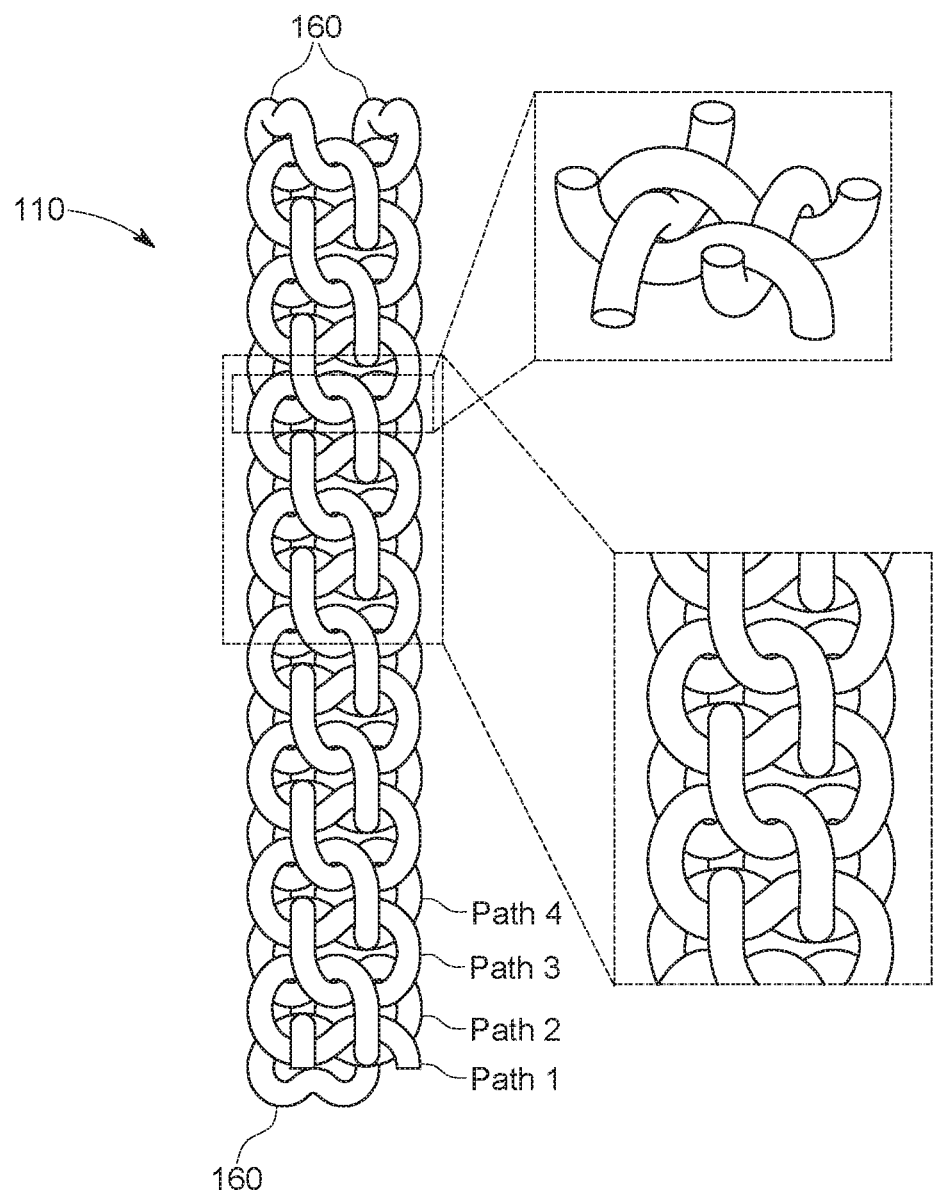
FIG. 3A is an isometric view of an exemplary continuous flow tube having four runs, according to an example of the present disclosure.
Figure 3B:
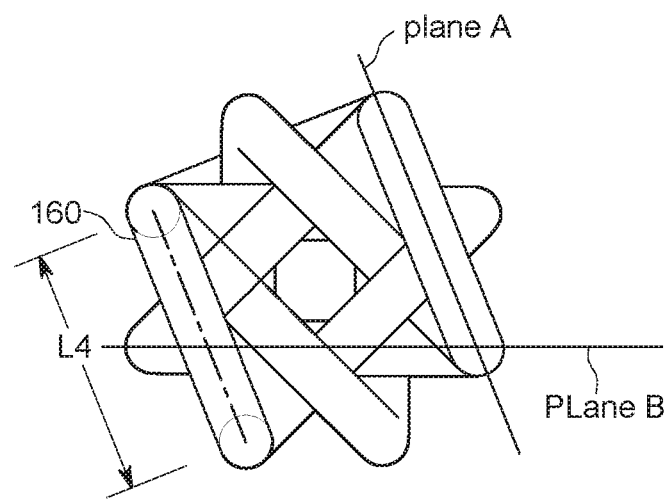
FIG. 3B is a top view of the exemplary continuous flow tube of FIG. 3A, according to an example of the present disclosure.

In an example, as shown in FIG. 2E, the continuous flow reactor tube 110 can include a first flow path having a plurality of turns 114 crating a first pattern that can be repeated a predetermined number of times, such as two times, and a second flow path that is substantially straight or includes a serpentine pattern between the turns of the first flow path. As can be seen from FIG. 2C, the pattern of the turns 114 in the first flow path creates a top view with an eight-pointed star. When the continuous flow reactor tube 110 includes a plurality of flow paths, such as four flow paths, as shown in FIG. 3A, each of the four flow paths can include turns and patterns that are substantially the same and can be interwoven and/or arranged to occupy spaces formed within each turn in each of the flow paths. Accordingly, the top view of the continuous flow reactor tube 110 weather having one flow path or four flow paths or more, will substantially look like an eight-pointed star, as shown in FIGS. 2C and 3B.

Figure 2F:
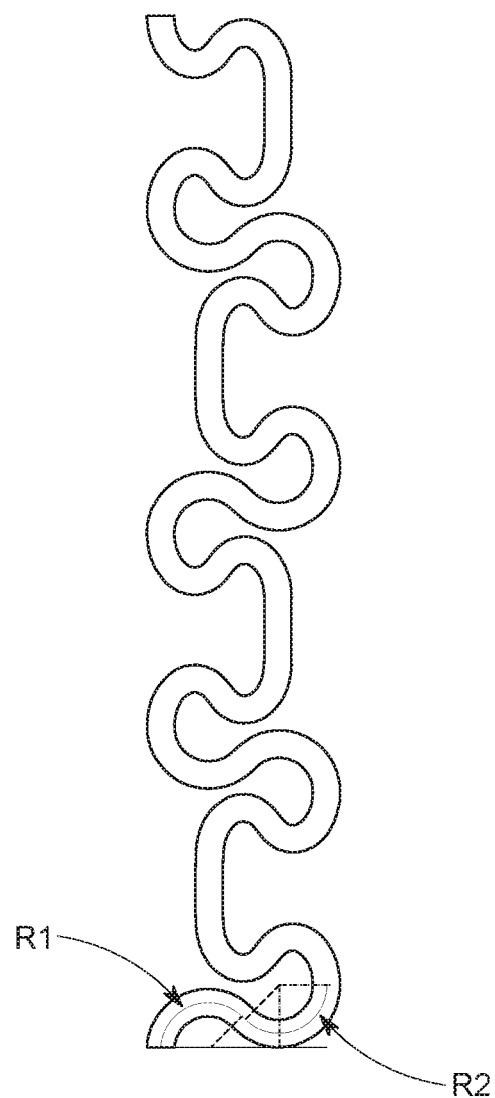
FIG. 2F is a side view of the exemplary continuous flow tube of FIG. 2A, according to an example of the present disclosure.
Figure 2G:
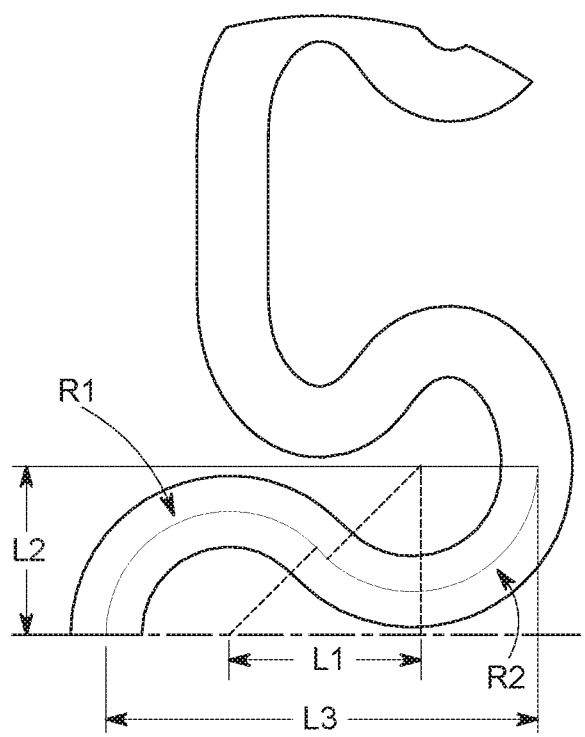
FIG. 2G is a detailed view of area A of the side view of the exemplary continuous flow tube of FIG. 2F, according to an example of the present disclosure.

Referring to FIGS. 2F and 2G, each of the turns 114 in the continuous flow reactor tube 110 can include a vertical L1 center to center distance between the turns of from about 1 cm to about 2 cm, such as about 1.5 cm. Additionally, each of the turns 114 can include a horizontal L2 center to center distance between the turns of from about 1 cm to about 2 cm, such as about 1.63 cm. Furthermore, each of the turns 114 can include an end to end distance L3 of from about 3 cm to about 4 cm, such as about 3.85 cm. The radius of each turn 114 in the continuous flow reactor tube 110 can be substantially constant. For example, referring to FIG. 2G, the radius R1 and R2 can be within 0.05 cm or less of each other, such as about 0.02 cm of each other to prevent substantial differences in the Dean Number between alternating turns. For example, R1 can be about 1.10 cm and R2 can be about 1.12 cm.

In an example, the plurality of flow paths can be interwoven such that the plurality of turns creates and multiaxial three-dimensional flow path. Such a multiaxial three-dimensional flow path can be arranged to create an overall shape of a sheet (as shown in FIGS. 4A-4C), prism (not shown in the Figs.), cylinder (as shown in FIG. 3A), cone (not shown in the Figs.), and/or sphere (not shown in the Figs.).

Figure 4A:
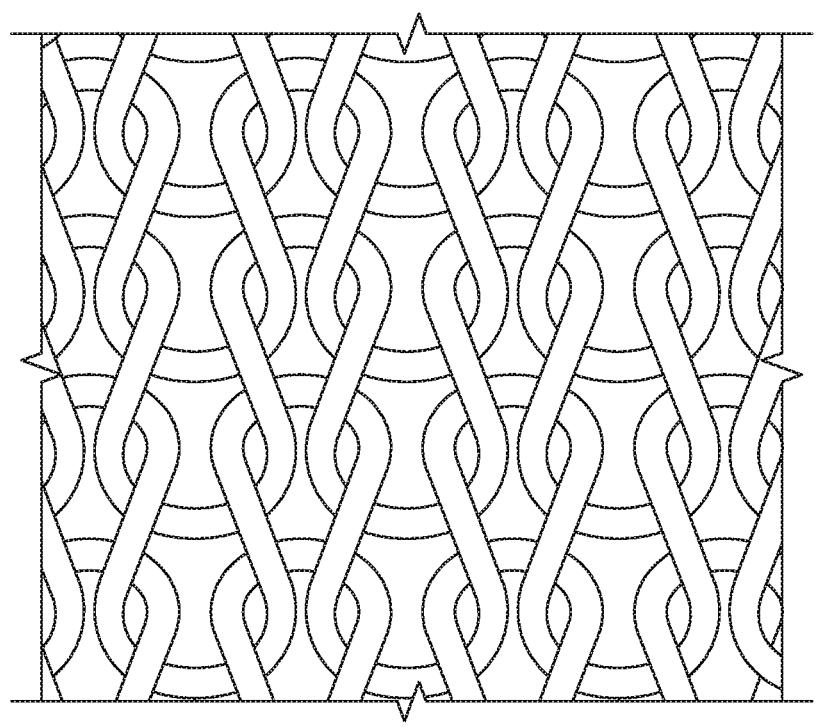
FIG. 4A illustrates first flow path and a second flow path having a weft-like pattern, according to an example of the present disclosure.
Figure 4B:
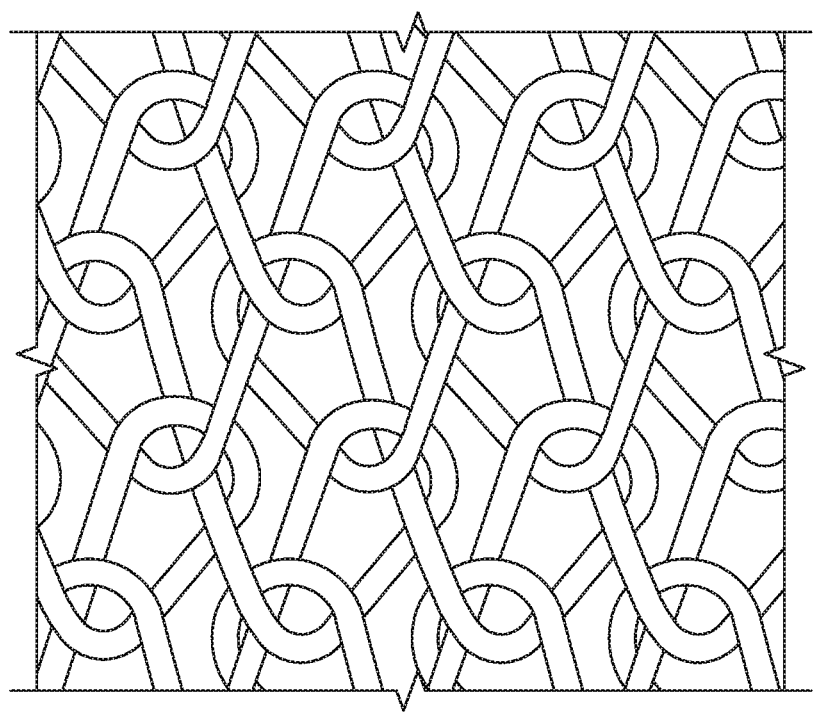
FIG. 4B illustrates a first flow path and a second flow path having a warp-like pattern, according to an example of the present disclosure.
Figure 4C:
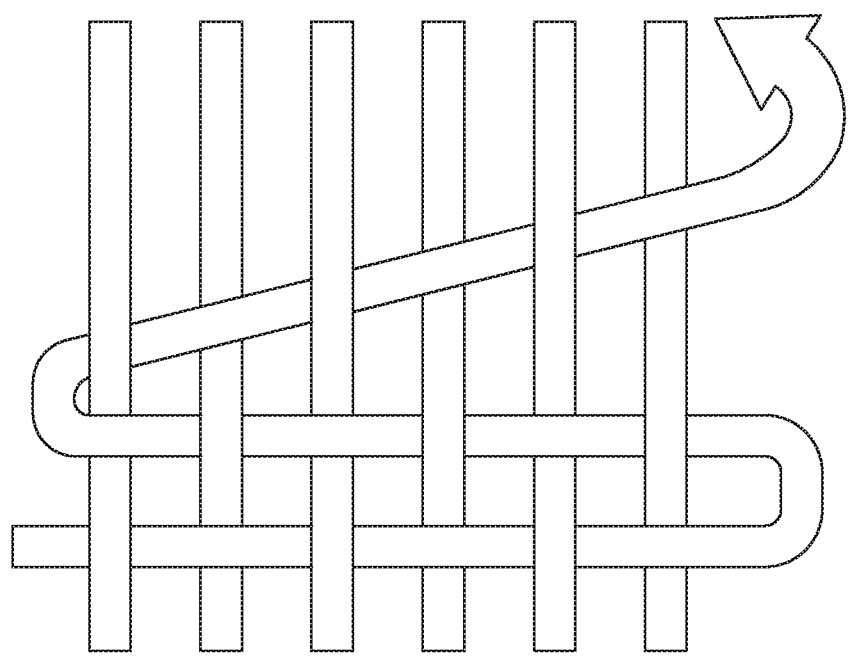
FIG. 4C illustrates a first flow path having a warp-like pattern and a second flow path having a weft-like pattern, according to an example of the present disclosure.

In an example, when the flow paths of the continuous flow reactor tube 110 are interwoven to create a sheet-like structure, the first flow path and the second flow path can include turns that create a weft-like pattern, as shown in FIG. 4A. Alternatively, the first flow path and the second flow path can include turns that create a warp-like pattern, as shown in FIG. 4B. Yet, in another example, the first flow path can include turns to create a weft-like pattern and the second flow path can include turns to create a warp-like pattern, as shown in FIG. 4C.

Material and Design of Continuous Flow Reactor Tube

The continuous flow reactor according to the invention can be made of any appropriate inert material, e.g. glass, synthetic material or metal. In another example, the continuous flow reactor tube 110 can be made of at least one flexible and/or memory alloy material. For example, the interwoven flow paths of the continuous flow reactor tube 110, as shown in FIG. 3A, can be made of memory alloy or flexible material. Such a material can allow a user of the continuous flow reactor tube 110 to change the shape of the tube and/or manipulate its flow rates as necessary without the need for designing a new reactor. For example, if the continuous flow reactor tube 110 needs to be heated in a hot bath, but the available hot bath cannot accommodate a rectangular shaped continuous flow reactor tube 110, then a user can change the shape of the continuous flow reactor tube 110, to a circular shape, to better fit it in the hot bath. Furthermore, using a flexible or memory alloy material for the continuous flow reactor tube 110 can allow a user to change the density of turns per square meter of the reactor. This allows a single reactor to be used for multiple purposes. Depending on the purpose of the reactor, a user can straighten some of the turns or add additional turns to the continuous flow reactor tube 110. In an example, the density of the 135° to 140° turns per volume of the reactor can be from about 19.6 turns/m³ to about 39.2 turns/m³.

Details of Interwoven Flow Path

Figure 3C:
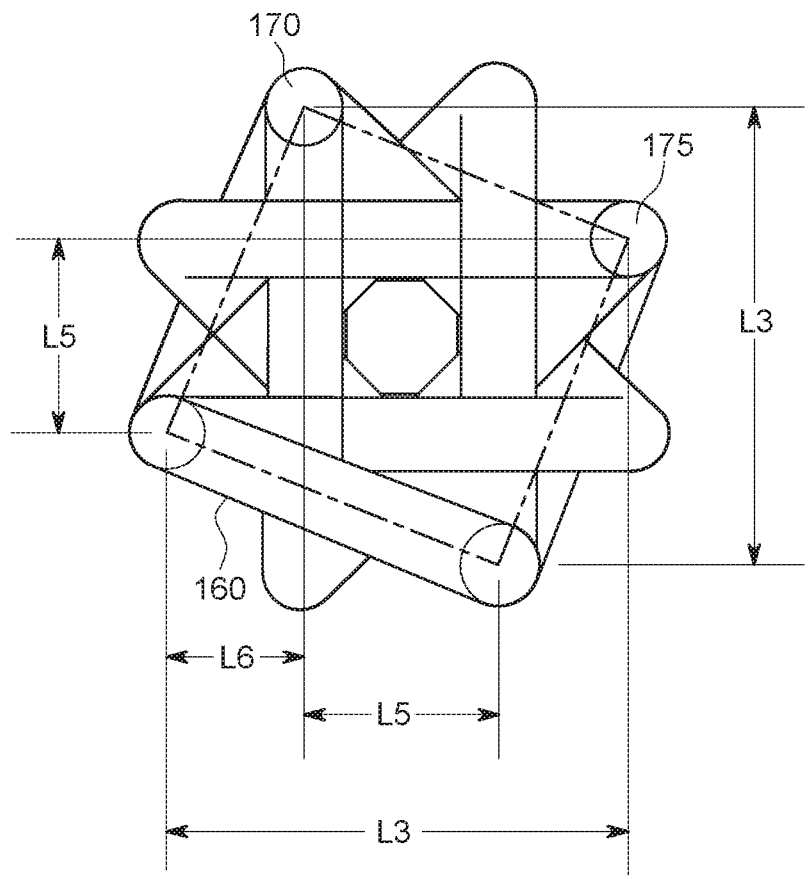
FIG. 3C is a bottom view of the exemplary continuous flow tube of FIG. 3A, according to an example of the present disclosure.
Figure 3D:
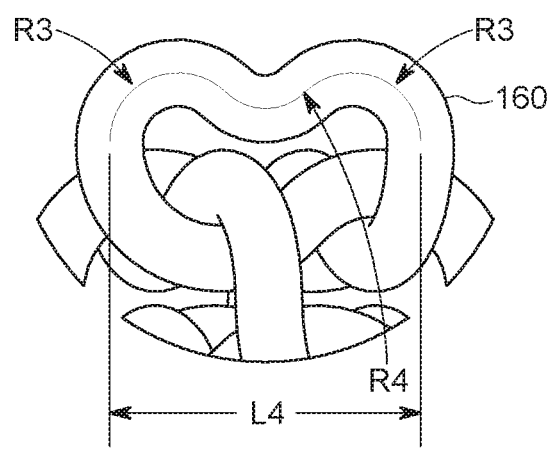
FIG. 3D is a detailed view of the connection point between first flow path and second flow path of the exemplary continuous flow tube of FIG. 3A, according to an example of the present disclosure.

FIGS. 3A-3D illustrate an exemplary design where the continuous flow reactor tube 110 can include a plurality of interwoven flow paths in fluid communication to create a single flow path. For example, FIG. 3A illustrates four paths (Paths 1-4), which are in fluid communication with one another to create a single flow path 112. This design can allow for a more compact design by reducing the distance required between the flow paths and the void space below the flow path, when compared to a linear pattern of stacking the flow paths side-by-side. FIG. 3A also illustrates a close-up of the weaving pattern of the four flow paths. In this example, Paths 1-4 are connected by curved connections, such as flow path connector 160, as shown in FIG. 3D, to avoid straightaways in the flow path.

In an example, as shown in FIGS. 3A and 3D, the flow path connector 160 can be a tube that appears to have two convex end area and a central concave area; thereby, creating an "m" like shape. Referring to FIG. 3D, the slope between the convex and the concave area can be at an angle of from about 30 degrees to about 60 degrees, such as an angle of about 45°. Furthermore, the radius R3 for each of the convex areas is from about 0.3 cm to about 0.9 cm, such as about 0.65 cm and the radius R4 for the concave area is from about 0.2 cm to about 0.8 cm, such as about 0.52 cm. Furthermore, as can be seen from FIGS. 3B and 3D, the distance L4, which is from the center of one end of the flow path connector 160 to the center of the second end of the flow path connector 160 can be from about 2 cm to about 4 cm, such as about 2.96 cm.

Referring to FIG. 3C, as stated above, the four flow paths will create a top and bottom view of an eight-pointed star. Referring to FIG. 3C, the eight-pointed star includes at least two vertical parallel tubes, two horizontal parallel tubes, and a flow path connector 160. Each of the turns 114 can include an end to end distance L3 of from about 3 cm to about 4 cm, such as about 3.85 cm. Additionally, the distance L5 between each of the parallel tubes is from about 1 cm to about 2 cm, such as about 1.65 cm. Furthermore, the distance L6 between an end of the flow path connector 160 and to a tube entry 170 or tube exit 175 can be from about 0.5 cm to about 1.5 cm, such as about 1.1 cm.

Multiple Reactors Connected in Series

Figure 5:
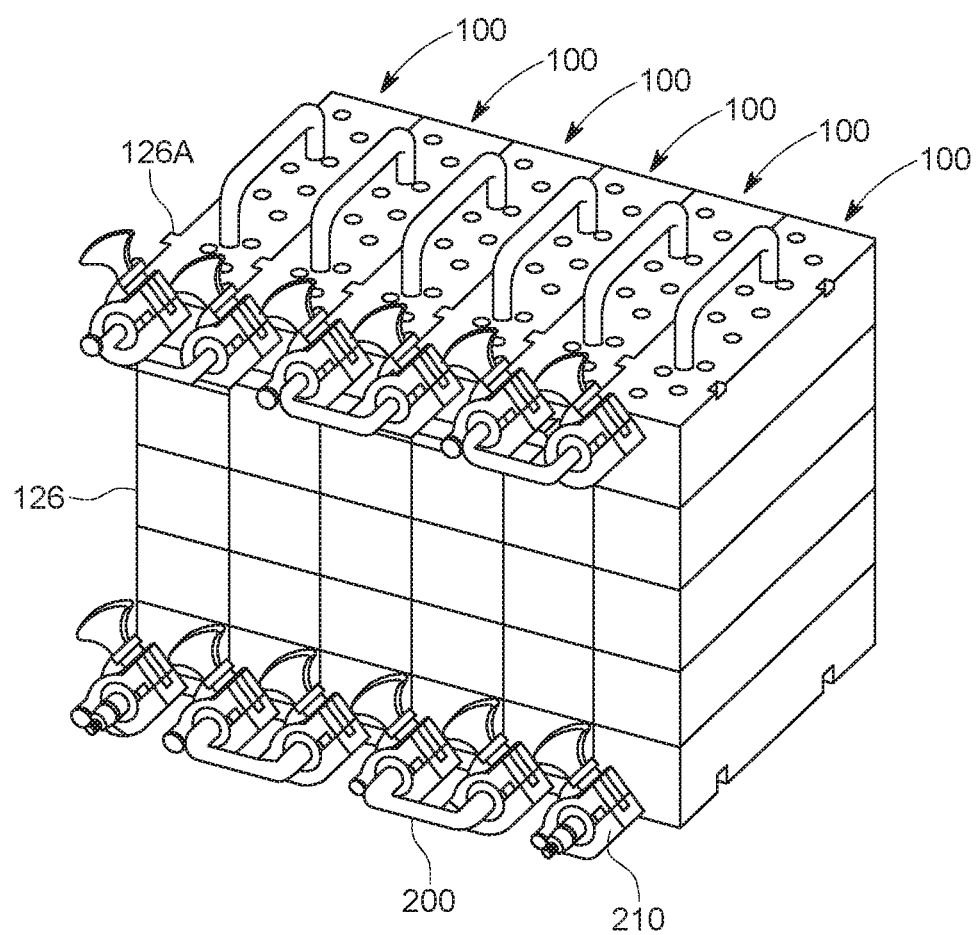
FIG. 5 illustrates a plurality of continuous flow reactor connected to one another, according to an example of the present disclosure.

In an example, as shown in FIG. 5, to allow for alterations to the path length and incubation time, in addition to the CVI reactor 100 having a plurality of layers 180, a plurality of CVI reactors 100 can be connected to one another in series. This can be accomplished by one or more flanged connectors. In an example, at least 2 tubular CVI reactors 100 can be connected to one another, such as at least 6 in-line tubular CVI reactors 100 or more. In this particular example, the tubular flow path 112 at each end of the CVI reactor 100 can partially extend out (extended section 190 from the CVI reactor 100. The extended section 190 can also include a flange 195, as shown in FIG. 1D. A connector 200 can include a horizontal 180° turn and/or be in a shape of a "U." One end of the connector can be connected to the tubular flow path 112 or the flange 195 of a first CVI reactor 100 and the second end of the connector can be connected to the tubular flow path 112 or the flange 195 of an adjacent in-line tubular CVI reactor 100.

The connector 200 can be connected to each tubular flow path 112 or flange 195 by a clamp 210 or by other fastener devices, such as a screw, an adhesive, etc. and/or integral connectors such as threaded male/female terminals, quick-connect/disconnect terminals, etc. In an example, a gasket can be placed between the end of the tubular flow path 112 or flange 195 and each end of the connector 200.

EXAMPLES

Example 1

Figure 6:
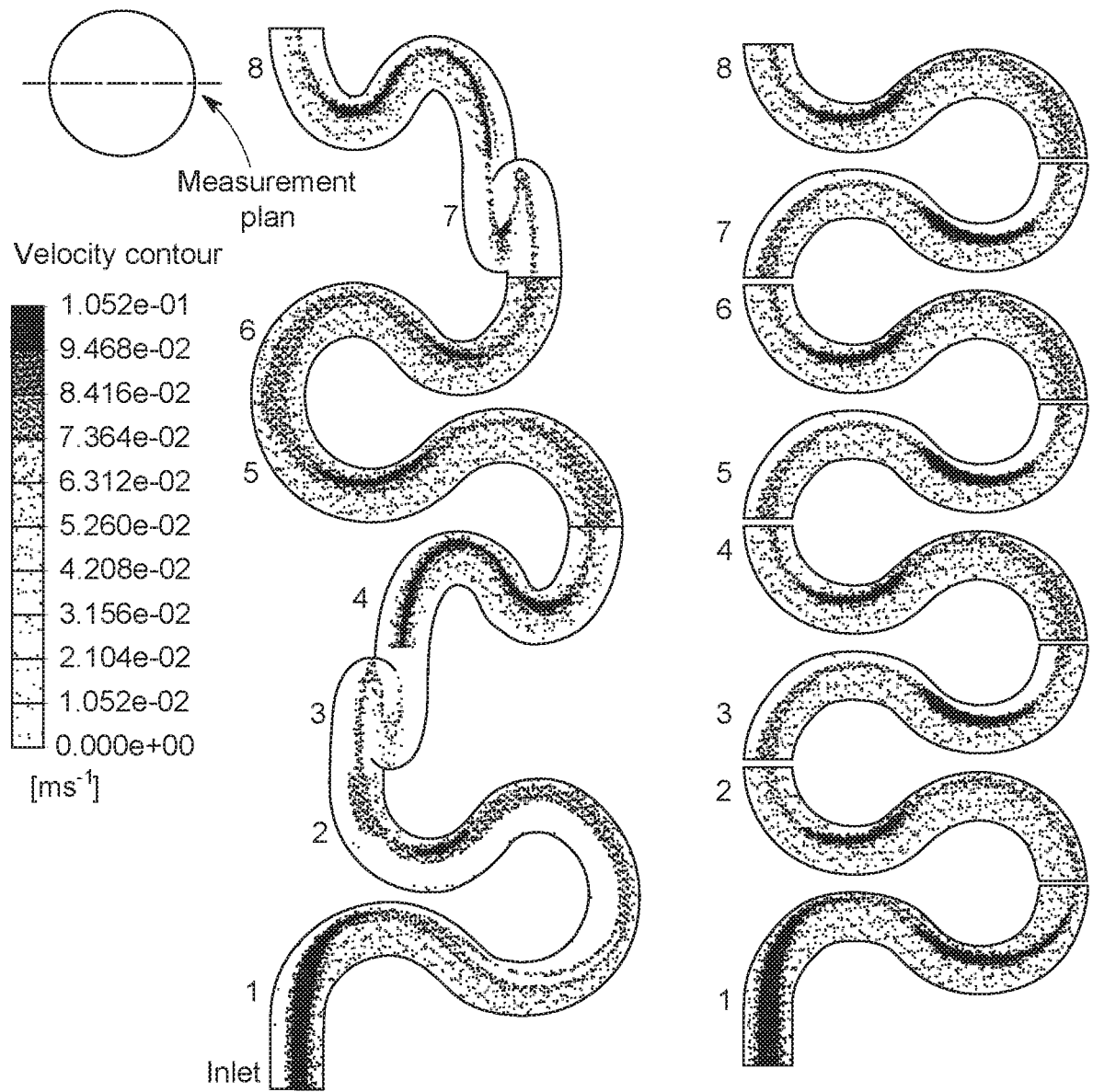
FIG. 6 illustrates a Centerline Velocity of the Weave Flow Path for an inlet velocity of $5.26E-02$ m s$^{-1}$, according to an example of the present disclosure.

The curvature of the flow in the CVI reactor 100, as shown in FIGS. 1A, 1C, and 1D, generated dean vortices to induce mixing while operating at a laminar flow regime. The 45° bends at the turn centers further increased mixing by changing the direction of the dean vortices generated by the turns. Referring to FIG. 6, the left side image illustrates the centerline velocity of the center plane flow path and the right side image illustrates all of the centerline planes for 16 135°-140° turns and 7 45° bends of the weave flow path. As seen in FIG. 6, the centerline velocity, measured at the center plane of the flow path, the profile varied with length despite operating at the laminar flow regime which is characterized by a parabolic velocity profile for fully developed flow. The characteristic parabolic velocity profile was seen at the inlet of the flow path, shown in FIG. 6, where the flow path was straight. Once the flow path shifted to weave flow path of alternating turns and bends, the centerline velocity profile changed dynamically with length.

Figure 7:
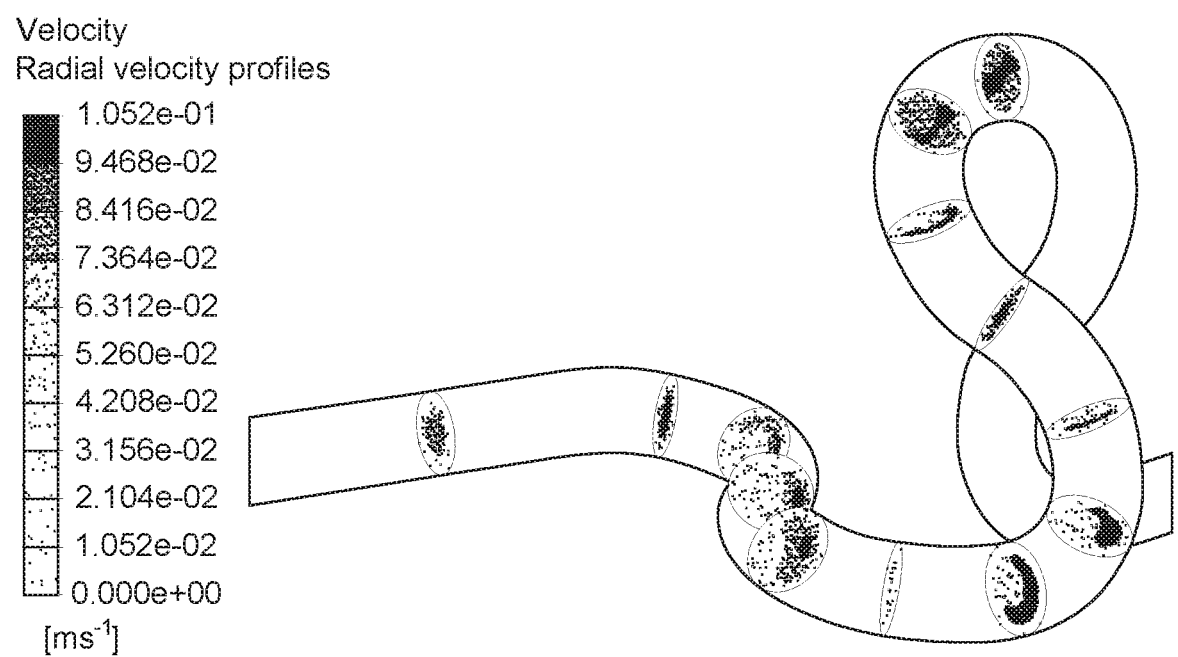
FIG. 7 illustrates a flow path and axial velocity contours along the weave flow path, according to an example of the present disclosure.
Figure 8:
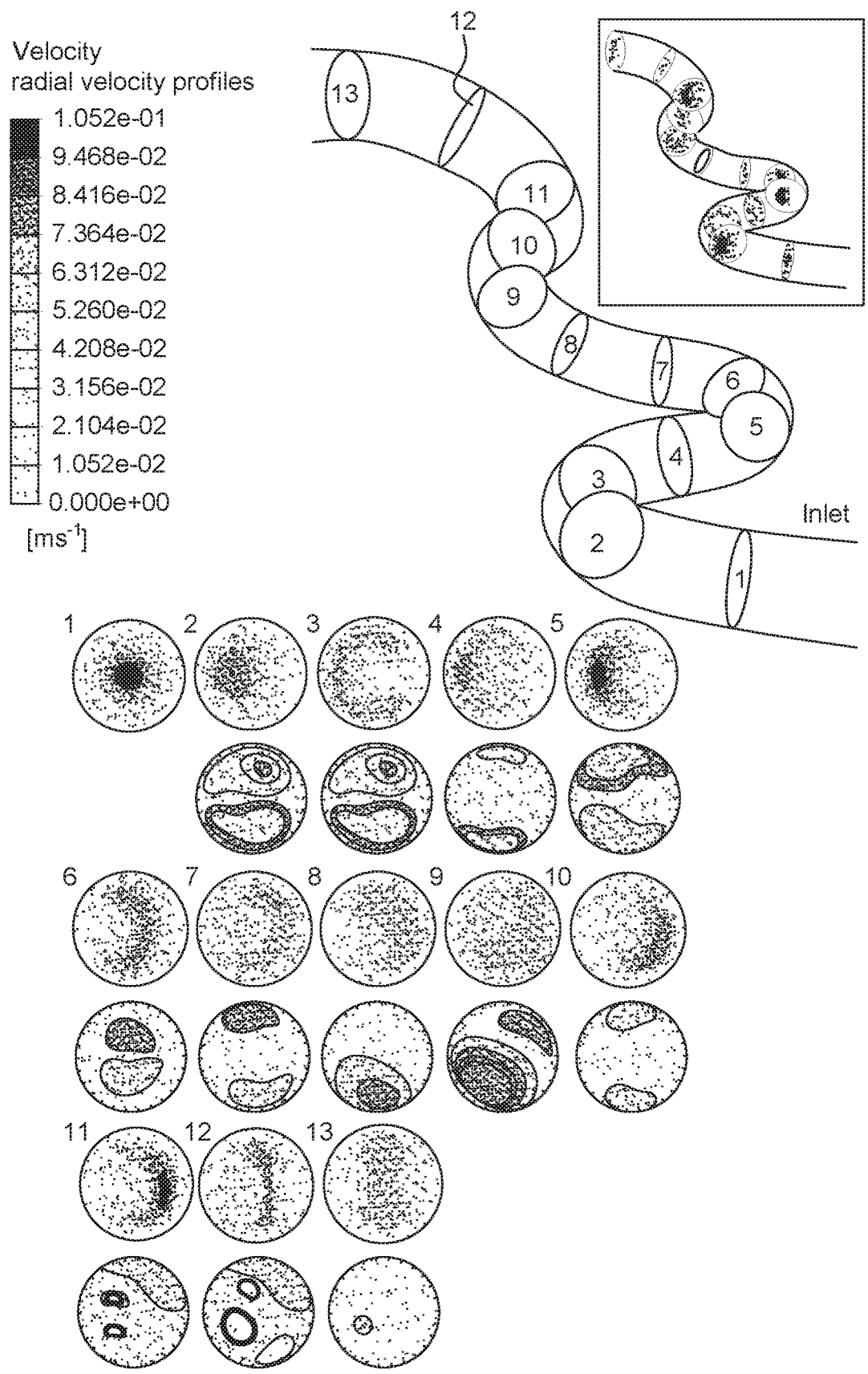
FIG. 8 illustrates the details of the Weave Design plane Velocity Contours and Dean Vortices/Radial Velocity of FIG. 7, according to an example of the present disclosure.

To further analyze the velocity profile of the weave design, axial velocity contours and Dean Vortices were measured at intervals 45° from the start of the alternating turns or approximately every 0.9 cm along the flow path, as shown in FIG. 7 and FIG. 8. In FIG. 8, the top image includes the velocity heat map and an overview of the planes where the axial velocities and radial velocities were measured along the flow path and are numbered 1-13. The inlet velocity was $5.26E-02$ m s$^{-1}$, which resulted in a maximum velocity of $1.052E-01$ m s$^{-1}$ for fully developed laminar flow. The velocity heat map ranged from 0 to $1.052E-01$ m s$^{-1}$. The bottom image is the flow path overview, the velocity contours (top) and radial velocities/Dean vortices (bottom), were measured at 13 planes located at the inlet and every 45° from the start of the turns along the flow path or approximately 0.9 cm spacing.

Figure 9:
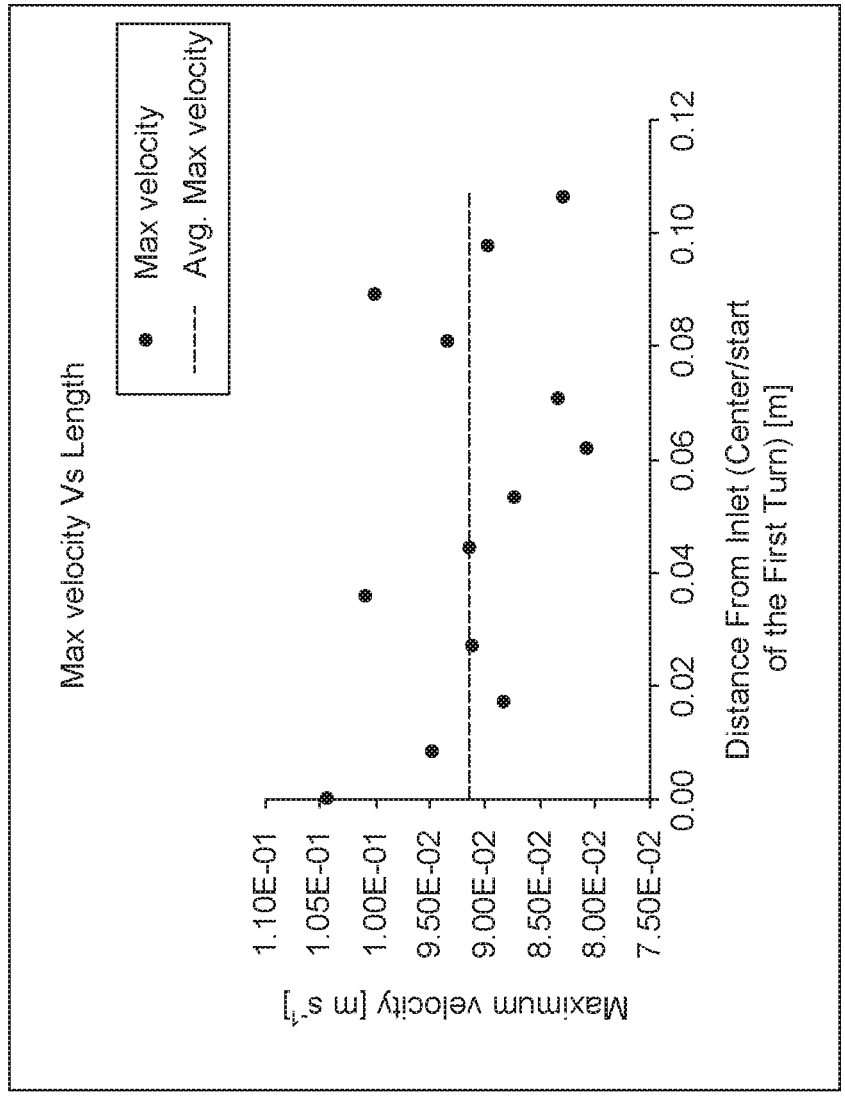
FIG. 9 illustrates the maximum velocities computed with an inlet velocity of $5.26 E-01$ m s$^{-1}$ as estimated for each of the radial planes in FIG. 8, according to an example of the present disclosure.
Figure 10A:
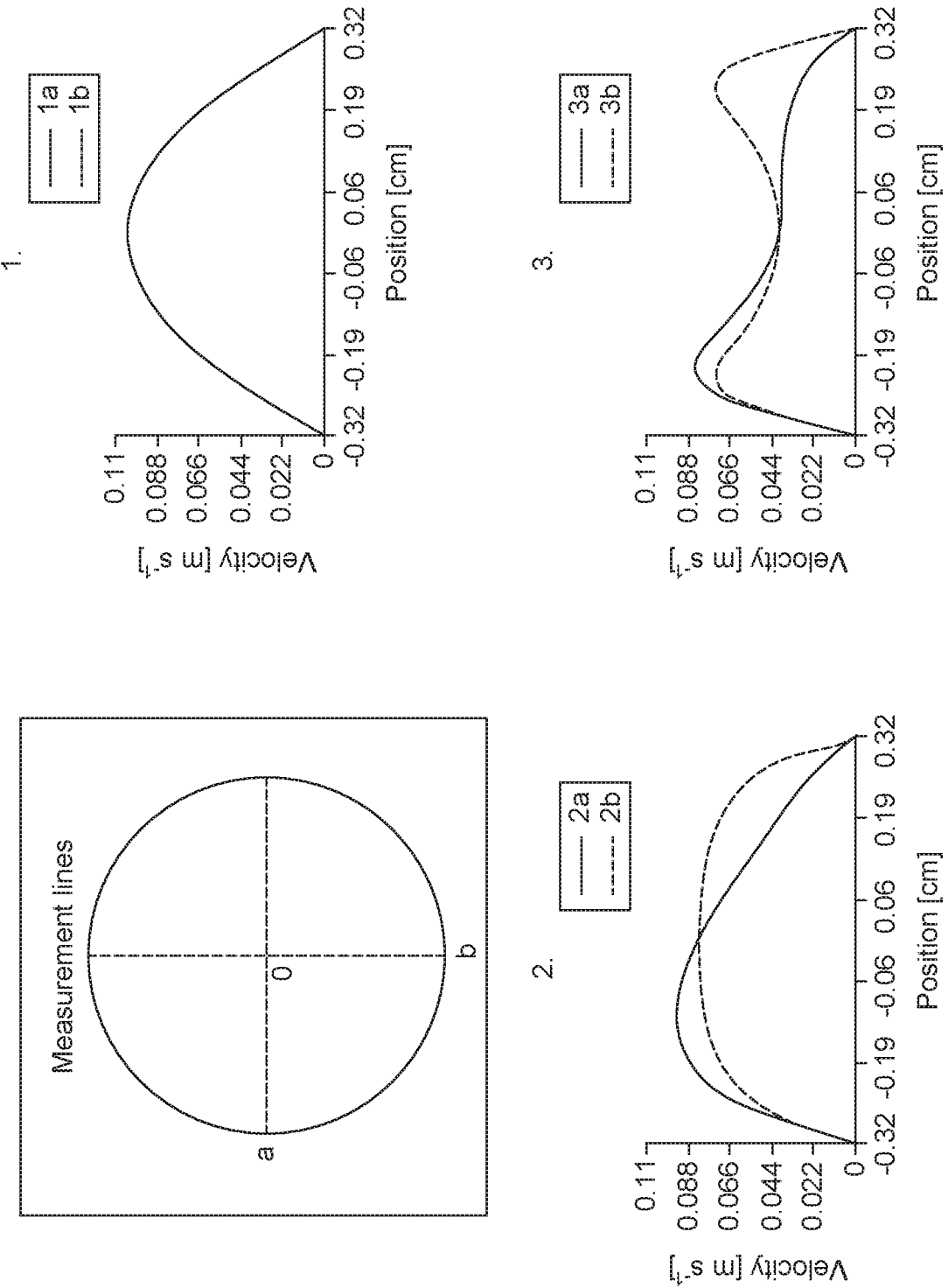
FIG. 10A illustrates the Horizontal and Vertical Centerline Velocities of the Radial Planes at positions 1-3 in FIG. 8, according to an example of the present disclosure.
Figure 10B:
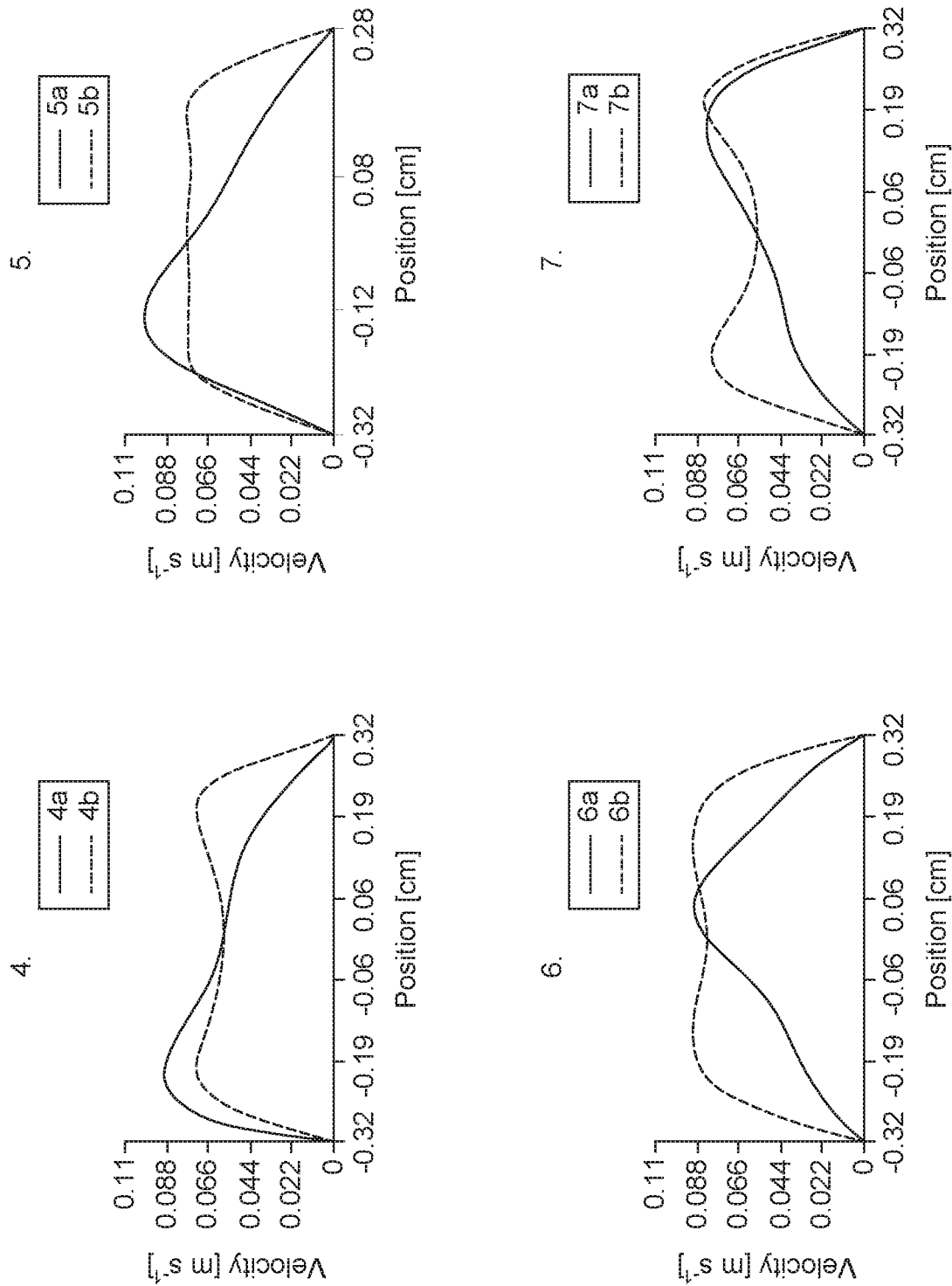
FIG. 10B illustrates the Horizontal and Vertical Centerline Velocities of the Radial Planes at positions 4-7 in FIG. 8, according to an example of the present disclosure.
Figure 10C:
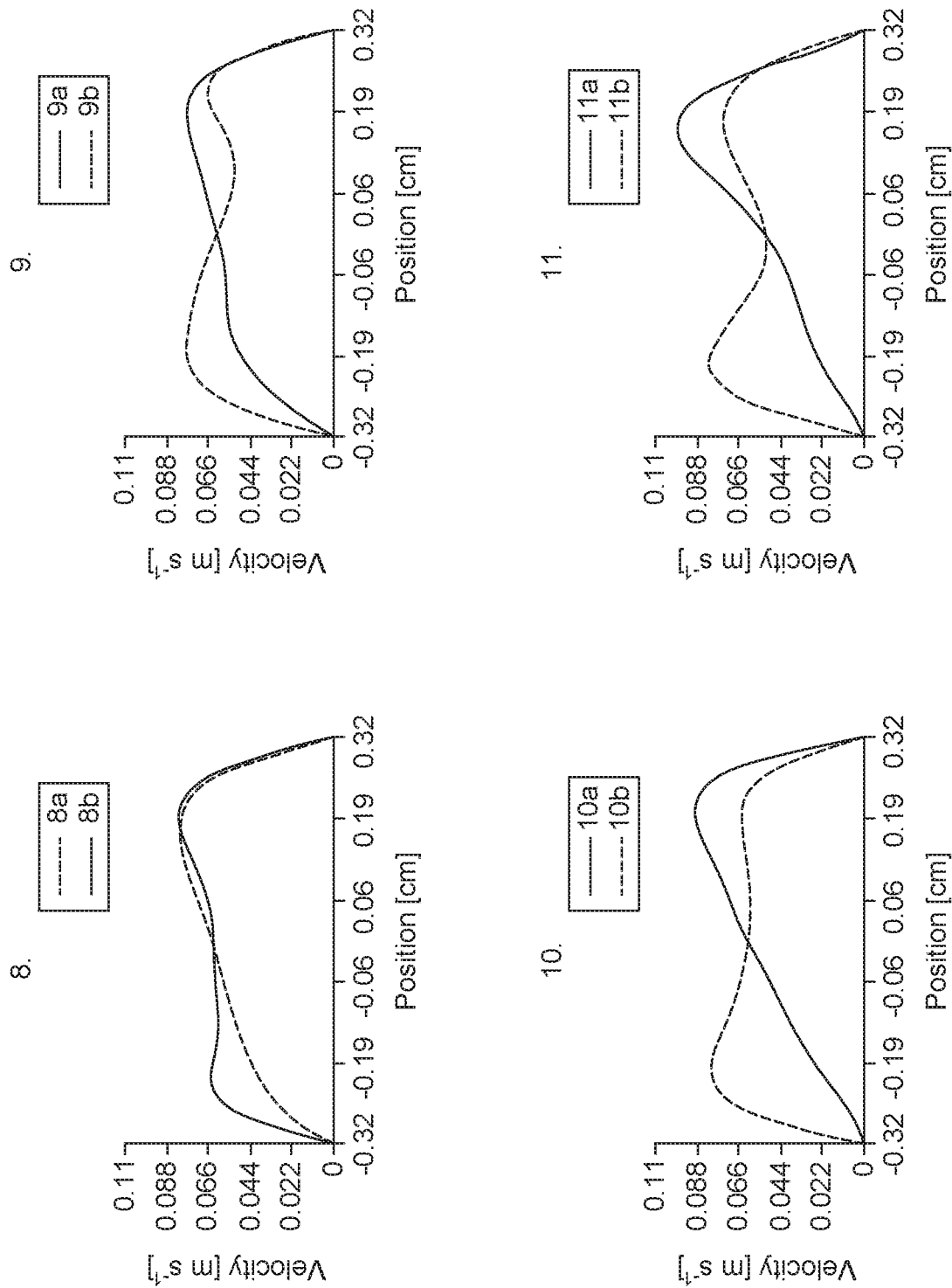
FIG. 10C illustrates the Horizontal and Vertical Centerline Velocities of the Radial Planes at positions 8-11 in FIG. 8, according to an example of the present disclosure.
Figure 10D:
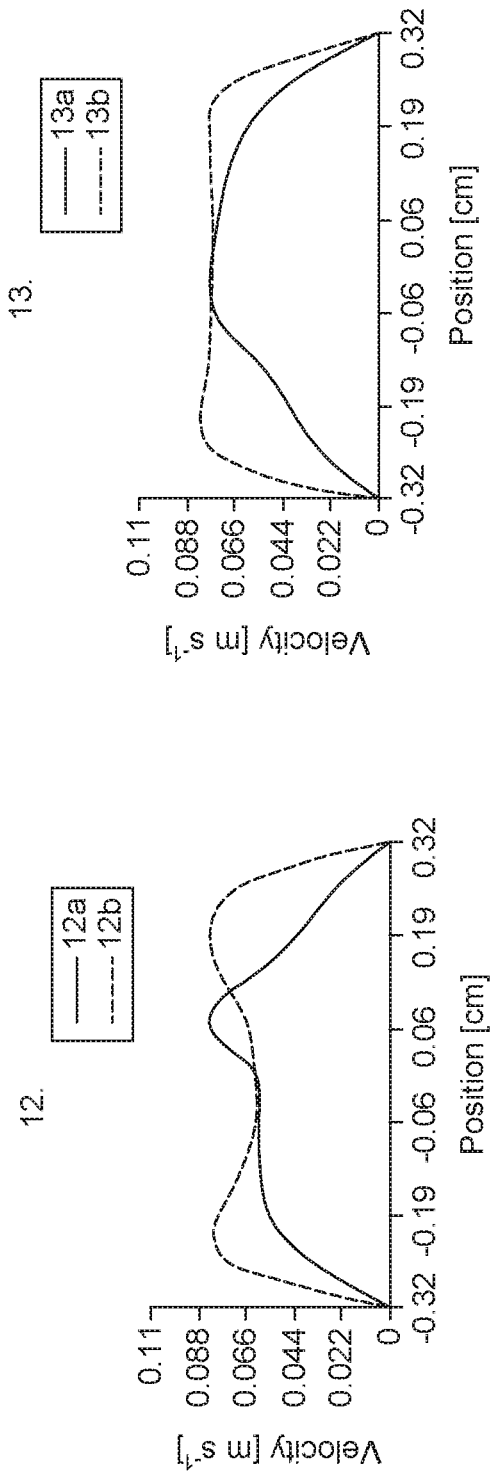
FIG. 10D illustrates the Horizontal and Vertical Centerline Velocities of the Radial Planes at positions 12-13 in FIG. 8, according to an example of the present disclosure.

The maximum velocity, for an average/inlet velocity of $5.26E-02$ m s$^{-1}$, at each plane in FIG. 8 was predicted and is given in the table and graph in FIG. 9. The characteristic value for laminar flow in a pipe of the maximum velocity was twice the average velocity ($2*v_{avg}$). Here our $v_{avg}$ was $5.26E-02$ m s$^{-1}$ and $2*v_{avg}$ was $1.052E-01$ m s$^{-1}$. At the inlet, before the curvature in the flow path, the max velocity reached the characteristic maximum value. However, for the radial planes within the weave flow path, the maximum velocities were lower than the characteristic value. This indicated that the flow path results in a lower maximum velocity and thus reduced axial dispersion.

For further analysis, the centerline velocity profiles, both horizontal and vertical of the radial planes in FIG. 8, is shown in FIG. 10. The characteristic symmetrical parabolic laminar flow velocity profile was again seen at the inlet; however, as the flow moved through the bends the profiles broadened and were non-symmetrical.

Example 2

Figure 11:
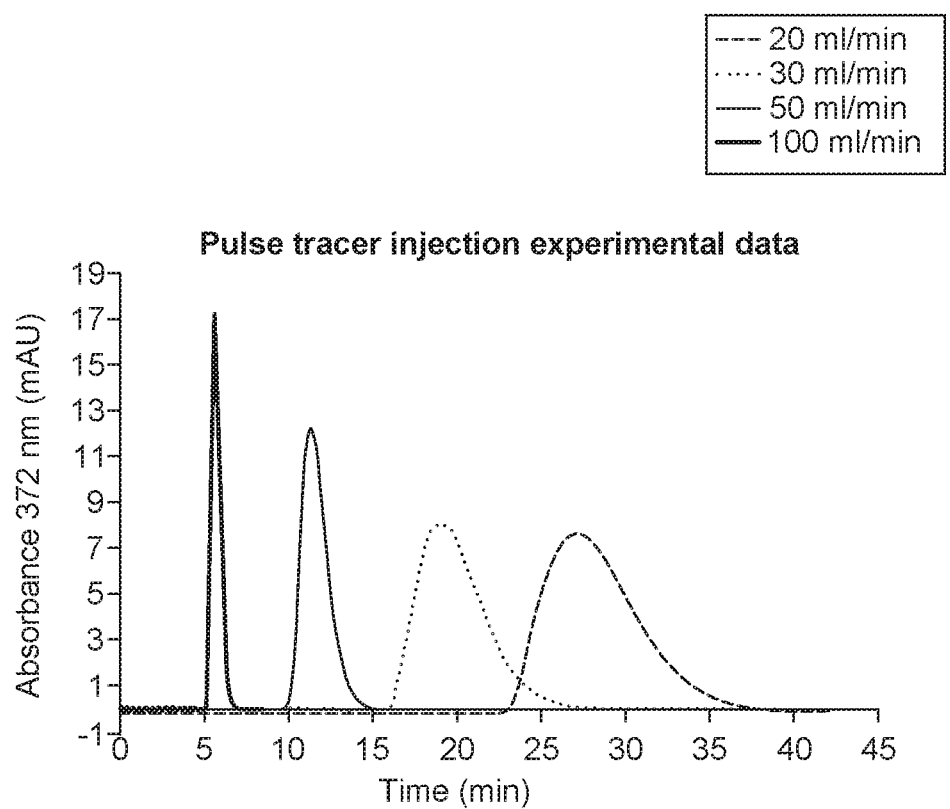
FIG. 11 is a graph illustrating the wave pulse tracer experimental data of absorbance at 372 nm vs time (min) for four flow rates 20, 30, 50, 100 ml/min (Linear Velocities of 1.05E-02, 1.58E-02, 2.63E-02, and 5.26E-02 m/s respectfully)

Pulse tracer experiments with the CVI Weave reactor consisted of first flushing the JIB with Milli-Q water, (Barnstead Nanopure Water Purification System, Thermo Scientific, Waltham, MA, USA), followed by a 13 ml pulse injection of 50 mg/ml Riboflavin, and finally chasing with Milli-Q water via a P-970 system pump on an ÄKTA Pilot (GE Healthcare, IL, USA). The absorbance of the tracer at the outlet was measured using a UV flow cell on an ÄKTA Pilot (GE Healthcare) at a wavelength of 372 nm. Results of the Absorbance vs. time from the pulse tracer experiments at four flow rates 20, 30, 40, 50, and 100 ml/min are shown in FIG. 11.

Laminar flow occurs at Reynolds Numbers (Re) less than 2000. The Re for flow in a pipe is defined by equation 1 below, where ρ is density, v is average velocity, d is the tube diameter, and μ is kinematic viscosity.

$$\text{Re} = \frac{\rho v d}{\mu} \quad (1)$$

For steady motion of an incompressible fluid in a curved pipe the strength of the secondary flows are characterized by a non-dimensional parameter, the Dean No (D), described by Eq. 2 where d is the tube inner diameter and R is radius of curvature of the flow path.

$$D = \text{Re}\sqrt{\frac{d}{2R}} \quad (2)$$

The RTD of the reactor can be represented such that the area under the curve is unity, E curve, and is defined by Eq. 3, where C is concentration of tracer at the outlet and t is time.

$$\int_0^\infty E(t)dt = \frac{C(t)}{\int_0^\infty C(t)dt} = 1 \quad (3)$$

Axial dispersion is characterized by the mean residence time, $\bar{t}$, and variance, $\sigma^2$, defined by Eq. 4 and Eq. 5 respectfully.

$$\bar{t} = \frac{\int_0^\infty t\, Cdt}{\int_0^\infty Cdt} \quad (4)$$

$$\sigma^2 = \frac{\int_0^\infty t^2 Cdt}{\int_0^\infty Cdt} - \bar{t}^2 \quad (5)$$

The following Table 1 gives the Reynolds Numbers (Re), Dean Numbers (D), and variance ($\sigma^2$) for the pulse tracer experiments shown in previously in FIG. 11. These values are critical to characterizing the mixing efficiency of our design as lower variance values closer to the variance of the injection pulse, indicate that the weave design reactor is approaching mixing closer to plug flow despite operating at the laminar flow regime where Re<2000. In the able the lowest value of variance is 0.1 min² at the highest flow rate of 100 ml/min.

TABLE 1

Experimental Pulse Tracer flow rates, linear velocity, variance, Reynolds Number, and Dean Number at four volumetric flow rates 20, 30, 50, and 100 ml/min

| Flow Rate (ml/min) | linear Velocity (m/s) | Variance (min²) | Reynolds No. | Dean No. |
|---|---|---|---|---|
| 20 | 1.05E−02 | 7.37 | 75.1 | 40.3 |
| 30 | 1.58E−02 | 4.62 | 112.6 | 60.5 |
| 50 | 2.63E−02 | 0.71 | 187.7 | 100.9 |
| 100 | 5.26E−02 | 0.10 | 375.5 | 201.7 |

The E curve can be expressed in dimensionless form, E(θ), as described in Eq. 6, where θ is dimensionless time and θ=t/$\bar{t}$. Variance can be expressed in dimensionless time by dividing the variance by the squared value of the mean residence time, $\sigma_\theta^2 = \sigma_t^2/\bar{t}^2$. The dimensionless E Curves for the experimental data in FIG. 11 is shown in the following FIG. 12. The more symmetrical and centered around one the dimensionless RTD curve is the closer the reactor is to preforming as a plug flow reactor.

Figure 12:
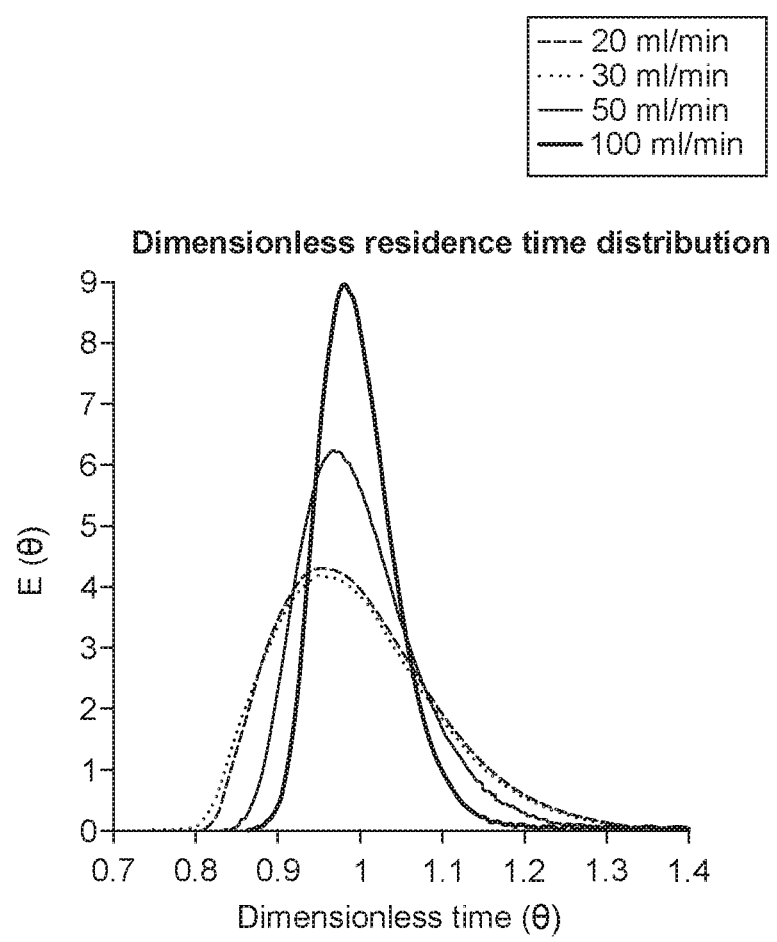
FIG. 12 is a graph illustrating dimensionless E Curves of Weave Pulse Tracer experiments at 20, 30, 50, and 100 ml/min.

As seen in FIG. 12, the dimensionless residence time distribution curves, E(Θ), for 20 ml/min is slightly more narrow than the 30 ml/min flow rate. This is characteristic of the secondary flows within the range of Dean Number values of D≤40~60 where the flow is unidirectional. At higher Dean Numbers D≥60 the Dean vortices become stable with pairs of vortices generated From the foregoing description, those skilled in the art can appreciate that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

The scope of this disclosure is to be broadly construed. It is intended that this disclosure disclose equivalents, means, systems, and methods to achieve the devices, activities and mechanical actions disclosed herein. For each device, article, method, mean, mechanical element or mechanism disclosed, it is intended that this disclosure also encompass in its disclosure and teaches equivalents, means, systems, and methods for practicing the many aspects, mechanisms and devices disclosed herein. Additionally, this disclosure regards a coating and its many aspects, features, and elements. Such a device can be dynamic in its use and operation, this disclosure is intended to encompass the equivalents, means, systems, and methods of the use of the device and/or article of manufacture and its many aspects consistent with the description and spirit of the operations and functions disclosed herein. The claims of this application are likewise to be broadly construed The description of the inventions herein in their many embodiments is merely exemplary in nature and, thus, variations that do not depart from the gist of the invention are intended to be within the scope of the invention. Such variations are not to be regarded as a departure from the spirit and scope of the invention.

We claim:
1. A continuous flow reactor comprising:
 a plurality of interwoven flow paths in fluid communication to form a single continuous flow reactor tube having a single flow path.

2. The continuous flow reactor of claim 1, wherein each of the plurality of interwoven flow paths comprises a plurality of turns that are in different, non-parallel planes.

3. The continuous flow reactor of claim 2, wherein the plurality of turns includes at least a first pattern and a second pattern different from the first pattern, wherein the first pattern includes a predetermined number of turns, and the second pattern includes a predetermined number of turns, and wherein the predetermined number of turns in the first pattern is same or different from the predetermined number of turns in the second pattern.

4. The continuous flow reactor of claim 2, wherein the plurality of turns includes a repeated pattern of turns.

5. The continuous flow reactor of claim 4, wherein the pattern of turns is repeated after 8 bends.

6. The continuous flow reactor of claim 2, wherein each of the plurality of turns includes an angle of from about 100° to about 200°.

7. The continuous flow reactor of claim 2, wherein each of the plurality of turns includes an angle of from about 135° to about 140°.

8. The continuous flow reactor of claim 2, wherein the plurality of turns follows a three-dimensional path that includes flow direction changes at approximately 45°, at a turn center.

9. The continuous flow reactor of claim 1, wherein the plurality of interwoven flow paths is made of at least one of flexible and memory alloy.

10. The continuous flow reactor of claim 1, wherein the plurality of interwoven flow paths includes from about 19.6 to about 39.2 turns per 1 $m^3$.

11. The continuous flow reactor of claim 1, wherein the plurality of interwoven flow paths includes internals.

12. The continuous flow reactor of claim 1, wherein the plurality of interwoven flow paths comprises a weft-like pattern and a warp-like pattern.

13. The continuous flow reactor of claim 1, wherein the plurality of interwoven flow paths comprises a plurality of bends each bend being rotated, with respect to one another, at an angle around a longitudinal axis of the plurality of interwoven flow paths.

14. The continuous flow reactor of claim 13, wherein the angle around the longitudinal axis of the interwoven flow path is from about 25 degrees to about 60 degrees.

15. A continuous flow reactor comprising:
a plurality of interwoven flow paths, wherein at least one flow path is on a single longitudinal axis and comprises a plurality of turns, wherein at least two of the plurality of turns are in different, non-parallel planes.

16. The continuous flow reactor of claim 15, wherein the plurality of turns includes a first pattern that is repeated a predetermined number of times.

17. The continuous flow reactor of claim 15, wherein the plurality of turns includes at least a first pattern and a second pattern different from the first pattern, wherein the first pattern includes a predetermined number of turns, and the second pattern includes a predetermined number of turns, and wherein the predetermined number of turns in the first pattern is same or different from the predetermined number of turns in the second pattern.

18. The continuous flow reactor of claim 15, wherein each of the plurality of turns is separated from one another by a bend having an angle smaller than an angle of the plurality of turns.

19. The continuous flow reactor of claim 18, wherein each of the bends includes an angle of less than about 135° and wherein each of the plurality of turns includes an angle of from about 135° to about 140°.

20. The continuous flow reactor of claim 15, wherein the plurality of interwoven flow paths comprises four flow paths interwoven with one another.

21. A method of viral inactivation in a continuous flow reactor comprising:
introducing a process stream and at least one virus inactivating compound or solution into a continuous flow reactor at a flow rate having a Reynolds number of from about 187 to about 333 and a Dean Number of from about 105 to about 212; and
contacting the process stream with the at least one virus inactivating compound or solution in the continuous flow reactor;
wherein the continuous flow reactor comprises:
(i) a plurality of interwoven flow paths in fluid communication to form a single continuous flow reactor tube having a single flow path; and/or
(ii) a plurality of interwoven flow paths, wherein at least one flow path is on a single longitudinal axis and comprises a plurality of turns, wherein at least two of the plurality of turns are in different, non-parallel planes.

\* \* \* \* \*